United States Patent
Rosenberg

(10) Patent No.: US 6,850,222 B1
(45) Date of Patent: *Feb. 1, 2005

(54) PASSIVE FORCE FEEDBACK FOR COMPUTER INTERFACE DEVICES

(75) Inventor: Louis B. Rosenberg, Pleasanton, CA (US)

(73) Assignee: Immersion Corporation, San Jose, CA (US)

( * ) Notice: Subject to any disclaimer, the term of this patent is extended or adjusted under 35 U.S.C. 154(b) by 179 days.

This patent is subject to a terminal disclaimer.

(21) Appl. No.: 09/603,758

(22) Filed: Jun. 26, 2000

Related U.S. Application Data

(63) Continuation of application No. 08/932,316, filed on Sep. 17, 1997, now Pat. No. 6,154,198, which is a continuation of application No. 08/400,233, filed on Mar. 3, 1995, now Pat. No. 5,767,839, which is a continuation-in-part of application No. 08/374,288, filed on Jan. 18, 1995, now Pat. No. 5,731,804.

(51) Int. Cl.⁷ ................................................ G09G 5/08
(52) U.S. Cl. ........................ 345/161; 345/156; 345/157
(58) Field of Search ................................ 345/161, 156, 345/157, 7; 74/471 XY; 434/45; 463/38; 273/148 B, 317

(56) References Cited

U.S. PATENT DOCUMENTS

| | | | |
|---|---|---|---|
| 2,906,179 A | 9/1959 | Bower | 90/13.5 |
| 2,972,140 A | 2/1961 | Hirsch | |
| 3,157,853 A | 11/1964 | Hirsch | |
| 3,220,121 A | 11/1965 | Cutler | |
| 3,490,059 A | 1/1970 | Paulsen et al. | 73/133 |
| 3,497,668 A | 2/1970 | Hirsch | |
| 3,517,446 A | 6/1970 | Corlyon et al. | |

(List continued on next page.)

FOREIGN PATENT DOCUMENTS

| | | |
|---|---|---|
| DE | 4400790 | 5/1995 |
| EP | 0085518 A1 | 8/1983 |
| EP | 0 349 086 A1 | 1/1990 |
| EP | 0626634 A2 | 5/1994 |
| GB | 2254411 | 10/1992 |
| GB | 2254911 | 10/1992 |
| JP | H2-185278 | 7/1990 |
| JP | H4-8381 | 1/1992 |

(List continued on next page.)

OTHER PUBLICATIONS

Schmult, Brian, et al., Application Areas for a Force–Feedback Joystick, 1993, DSC–vol. 49, Advances in Robotics, Mechatronics, and Haptic Interfaces.

(List continued on next page.)

*Primary Examiner*—Kent Chang

(57) ABSTRACT

A method and apparatus for interfacing the motion of an object with a digital processing system includes a sensor which has a sensing resolution and detects movement of the object along a degree of freedom. An amount of play less than the sesning resolution exists between the sensor and the object. A passive actuator is coupled to the mechanism to transmit a resistive force to the object along the degree of freedom. A play mechanism is coupled to the actuator to provide a desired amount of play between the actuator and the object along the degree of freedom. The desired amount of play is greater than the sensing resolution of the sensor so that the sensor can detect the desired play when the user moves the object, even when the actuator has locked the object into place. Such desired play can be torsion flex (compliance) or rotary backlash. The actuator and the sensor provide an electromechanical interface between the object and the digital processing system. A gimbal mechanism or slotted yoke mechanism can be coupled between the actuator and the object. The interface is well suited for simulations of medical procedures and simulations in which an object such as a stylus or a joystick is moved and manipulated by the user.

26 Claims, 18 Drawing Sheets

U.S. PATENT DOCUMENTS

| | | |
|---|---|---|
| 3,531,868 A | 10/1970 | Stevenson |
| 3,623,064 A | 11/1971 | Kagan |
| 3,795,150 A | 3/1974 | Eckhardt ..................... 74/5.4 |
| 3,875,488 A | 4/1975 | Crocker et al. |
| 3,890,958 A | 6/1975 | Fister et al. |
| 3,902,687 A | 9/1975 | Hightower |
| 3,903,614 A | 9/1975 | Diamond ..................... 35/12 |
| 3,911,416 A | 10/1975 | Feder |
| 3,919,691 A | 11/1975 | Noll ..................... 340/172.5 |
| 3,944,798 A | 3/1976 | Eaton ..................... 235/151.3 |
| 4,127,752 A | 11/1978 | Lowthorp |
| 4,148,014 A | 4/1979 | Burson ..................... 340/709 |
| 4,160,508 A | 7/1979 | Frosch et al. |
| 4,216,467 A | 8/1980 | Colston ..................... 340/365 L |
| 4,228,386 A | 10/1980 | Griffith ..................... 318/628 |
| 4,236,325 A | 12/1980 | Hall et al. |
| 4,262,549 A | 4/1981 | Schwellenbach |
| 4,333,070 A | 6/1982 | Barnes |
| 4,391,282 A | 7/1983 | Ando et al. ..................... 128/660 |
| 4,398,889 A | 8/1983 | Lam et al. ..................... 434/45 |
| 4,436,188 A | 3/1984 | Jones |
| 4,448,083 A | 5/1984 | Hayashi ..................... 73/862.04 |
| 4,464,117 A | 8/1984 | Foerst |
| 4,477,043 A | 10/1984 | Repperger ..................... 244/223 |
| 4,477,973 A | 10/1984 | Davies |
| 4,484,191 A | 11/1984 | Vavra |
| 4,489,304 A | 12/1984 | Hayes ..................... 338/128 |
| 4,513,235 A | 4/1985 | Acklam et al. |
| 4,550,221 A | 10/1985 | Mabusth |
| 4,550,617 A | 11/1985 | Fraignier et al. ......... 73/862.04 |
| 4,560,983 A | 12/1985 | Williams ..................... 340/825 |
| 4,571,834 A | 2/1986 | Fraser et al. |
| 4,581,491 A | 4/1986 | Boothroyd |
| 4,593,470 A | 6/1986 | Davies |
| 4,599,070 A | 7/1986 | Hladky et al. |
| 4,601,206 A | 7/1986 | Watson ..................... 73/514 |
| 4,604,016 A | 8/1986 | Joyce ..................... 414/7 |
| 4,632,341 A | 12/1986 | Repperger et al. ........... 244/230 |
| 4,638,798 A | 1/1987 | Shelden et al. ........ 128/303 B |
| 4,653,011 A | 3/1987 | Iwano |
| 4,654,648 A | 3/1987 | Herrington et al. ......... 340/710 |
| 4,676,002 A | 6/1987 | Slocum |
| 4,679,331 A | 7/1987 | Koontz |
| 4,688,983 A | 8/1987 | Lindbom |
| 4,689,449 A | 8/1987 | Rosen ..................... 200/6 A |
| 4,703,443 A | 10/1987 | Moriyasu |
| 4,704,909 A | 11/1987 | Grahn et al. ............. 73/862.04 |
| 4,708,656 A | 11/1987 | de Vries et al. |
| 4,712,971 A | 12/1987 | Fyler ..................... 414/744.5 |
| 4,713,007 A | 12/1987 | Alban |
| 4,750,487 A | 6/1988 | Zanetti |
| 4,769,763 A | 9/1988 | Trieb |
| 4,782,327 A | 11/1988 | Kley et al. ..................... 340/365 |
| 4,787,051 A | 11/1988 | Olson ..................... 364/518 |
| 4,791,934 A | 12/1988 | Brunnett |
| 4,794,392 A | 12/1988 | Selinko |
| 4,798,919 A | 1/1989 | Miessler et al. |
| 4,800,721 A | 1/1989 | Cemenska et al. ............. 60/393 |
| 4,803,413 A | 2/1989 | Kendig et al. |
| 4,811,608 A | 3/1989 | Hilton ..................... 73/862.04 |
| 4,819,195 A | 4/1989 | Bell et al. |
| 4,823,634 A | 4/1989 | Culver ..................... 74/471 |
| 4,831,531 A | 5/1989 | Adams et al. ......... 364/424.01 |
| 4,839,838 A | 6/1989 | LaBiche et al. ....... 364/709.11 |
| 4,849,692 A | 7/1989 | Blood |
| 4,861,269 A | 8/1989 | Meenen, Jr. ................. 434/45 |
| 4,879,556 A | 11/1989 | Duimel ..................... 341/20 |
| 4,885,565 A | 12/1989 | Embach |
| 4,888,877 A | 12/1989 | Enderle et al. |
| 4,891,764 A | 1/1990 | McIntosh |
| 4,891,889 A | 1/1990 | Tomelleri |
| 4,907,970 A | 3/1990 | Meenen, Jr. ................. 434/45 |
| 4,907,973 A | 3/1990 | Hon ..................... 434/262 |
| 4,930,770 A | 6/1990 | Baker |
| 4,934,694 A | 6/1990 | McIntosh |
| 4,942,545 A | 7/1990 | Sapia |
| 4,945,305 A | 7/1990 | Blood |
| 4,945,501 A | 7/1990 | Bell et al. |
| 4,949,119 A | 8/1990 | Moncrief et al. ........... 364/578 |
| 4,961,038 A | 10/1990 | MacMinn ................. 318/696 |
| 4,961,138 A | 10/1990 | Gorniak ..................... 364/200 |
| 4,961,267 A | 10/1990 | Herzog |
| 4,962,448 A | 10/1990 | DeMaio et al. ............. 364/146 |
| 4,962,591 A | 10/1990 | Zeller et al. |
| 4,982,504 A | 1/1991 | Soderberg et al. |
| 4,983,786 A | 1/1991 | Stevens et al. |
| 5,007,085 A | 4/1991 | Greanias et al. ............. 380/25 |
| 5,007,300 A | 4/1991 | Siva ..................... 74/471 XY |
| 5,019,761 A | 5/1991 | Kraft |
| 5,022,384 A | 6/1991 | Freels et al. |
| 5,022,407 A | 6/1991 | Horch et al. |
| 5,035,242 A | 7/1991 | Franklin et al. |
| 5,038,089 A | 8/1991 | Szakaly |
| 5,040,306 A | 8/1991 | McMurtry et al. |
| 5,044,956 A | 9/1991 | Behensky et al. ............. 434/45 |
| 5,050,608 A | 9/1991 | Watanabe et al. |
| 5,072,361 A | 12/1991 | Davis et al. ........... 364/167.01 |
| 5,076,517 A | 12/1991 | Ferranti et al. ............. 244/228 |
| 5,078,152 A | 1/1992 | Bond et al. |
| 5,088,055 A | 2/1992 | Oyama |
| 5,095,303 A | 3/1992 | Clark et al. ................. 340/710 |
| 5,103,404 A | 4/1992 | McIntosh ............... 318/568.22 |
| 5,107,080 A | 4/1992 | Rosen ..................... 200/6 A |
| 5,116,051 A | 5/1992 | Moncrief et al. ........ 273/448 B |
| 5,116,180 A | 5/1992 | Fung et al. ..................... 414/5 |
| 5,126,948 A | 6/1992 | Mitchell et al. ........ 364/474.03 |
| 5,128,671 A | 7/1992 | Thomas, Jr. ................. 341/20 |
| 5,131,844 A | 7/1992 | Marinaccio et al. |
| 5,132,672 A | 7/1992 | Clark |
| 5,139,261 A | 8/1992 | Openiano |
| 5,142,506 A | 8/1992 | Edwards ..................... 367/127 |
| 5,142,931 A | 9/1992 | Menahem ............... 74/471 XY |
| 5,143,505 A | 9/1992 | Burdea et al. ................. 414/5 |
| 5,146,566 A | 9/1992 | Hollis, Jr. et al. .......... 395/275 |
| 5,148,377 A | 9/1992 | McDonald |
| 5,156,363 A | 10/1992 | Cizewski et al. ........... 244/223 |
| 5,165,897 A | 11/1992 | Johnson |
| 5,175,459 A | 12/1992 | Danial et al. |
| 5,178,012 A | 1/1993 | Culp |
| 5,181,181 A | 1/1993 | Glynn ..................... 364/566 |
| 5,182,557 A | 1/1993 | Lang |
| 5,184,306 A | 2/1993 | Erdman et al. |
| 5,184,319 A | 2/1993 | Kramer ..................... 364/806 |
| 5,185,561 A | 2/1993 | Good et al. ................. 318/432 |
| 5,186,695 A | 2/1993 | Mangseth et al. |
| 5,187,874 A | 2/1993 | Takahashi et al. |
| 5,189,806 A | 3/1993 | McMurtry et al. |
| 5,193,963 A | 3/1993 | McAffee et al. ................. 414/5 |
| 5,197,003 A | 3/1993 | Moncrief et al. ........... 364/410 |
| 5,204,824 A | 4/1993 | Fujimaki |
| 5,209,131 A | 5/1993 | Baxter ..................... 73/865.8 |
| 5,212,473 A | 5/1993 | Louis |
| 5,220,260 A | 6/1993 | Schuler ..................... 318/561 |
| 5,223,776 A | 6/1993 | Radke et al. ............. 318/568.1 |
| 5,228,356 A | 7/1993 | Chuang ..................... 74/471 XY |
| 5,230,623 A | 7/1993 | Guthrie et al. ................. 433/72 |
| 5,235,868 A | 8/1993 | Culver ............... 745/471 XY |
| 5,240,417 A | 8/1993 | Smithson et al. |
| 5,243,266 A | 9/1993 | Kasagami et al. ........ 318/568.1 |
| 5,251,127 A | 10/1993 | Raab ..................... 364/413.13 |
| 5,251,156 A | 10/1993 | Heier et al. |

| | | |
|---|---|---|
| 5,259,120 A | 11/1993 | Chapman et al. |
| 5,259,894 A | 11/1993 | Sampson |
| 5,262,777 A | 11/1993 | Low et al. |
| 5,264,768 A | 11/1993 | Gregory et al. ............. 318/561 |
| 5,271,290 A | 12/1993 | Fischer |
| 5,275,174 A | 1/1994 | Cook |
| 5,275,565 A | 1/1994 | Moncrief ..................... 434/29 |
| 5,283,970 A | 2/1994 | Aigner |
| 5,286,203 A | 2/1994 | Fuller et al. .................. 434/45 |
| 5,296,846 A | 3/1994 | Ledley ....................... 345/161 |
| 5,299,810 A | 4/1994 | Pierce et al. |
| 5,309,140 A | 5/1994 | Everett, Jr. et al. |
| 5,334,027 A | 8/1994 | Wherlock |
| 5,351,692 A | 10/1994 | Dow et al. |
| 5,354,162 A | 10/1994 | Burdea et al. ................. 414/5 |
| 5,368,484 A | 11/1994 | Copperman et al. .......... 434/69 |
| 5,379,663 A | 1/1995 | Hara ..................... 74/471 XY |
| 5,381,080 A | 1/1995 | Schnell et al. ............. 318/566 |
| 5,384,460 A | 1/1995 | Tseng .................... 250/231.14 |
| 5,389,865 A | 2/1995 | Jacobus et al. ........ 318/568.11 |
| 5,390,296 A | 2/1995 | Crandall et al. |
| 5,396,266 A | 3/1995 | Brimhall ..................... 345/161 |
| 5,396,267 A | 3/1995 | Bouton |
| 5,397,323 A | 3/1995 | Taylor et al. |
| 5,397,865 A | 3/1995 | Park ............................ 178/18 |
| 5,402,582 A | 4/1995 | Raab ........................... 33/503 |
| 5,405,152 A | 4/1995 | Katanics et al. ............. 273/438 |
| 5,412,880 A | 5/1995 | Raab ........................... 33/503 |
| 5,414,337 A | 5/1995 | Schuler ...................... 318/561 |
| 5,417,696 A | 5/1995 | Kashuba et al. |
| 5,429,140 A | 7/1995 | Burdea et al. ............. 128/774 |
| 5,436,542 A | 7/1995 | Petelin et al. |
| 5,436,622 A | 7/1995 | Gutman et al. |
| 5,436,640 A | 7/1995 | Reeves ....................... 345/161 |
| 5,437,607 A | 8/1995 | Taylor |
| 5,445,166 A | 8/1995 | Taylor ....................... 128/897 |
| 5,459,382 A | 10/1995 | Jacobus et al. ........ 318/568.11 |
| 5,466,213 A | 11/1995 | Hogan et al. |
| 5,467,763 A | 11/1995 | McMahon et al. |
| 5,473,235 A | 12/1995 | Lance et al. ................ 318/561 |
| 5,512,919 A | 4/1996 | Araki |
| 5,513,100 A | 4/1996 | Parker et al. .......... 364/167.01 |
| 5,541,379 A | 7/1996 | Kim ........................... 200/566 |
| 5,547,382 A | 8/1996 | Yamasaki et al. |
| 5,575,761 A | 11/1996 | Hajianpour |
| 5,576,727 A | 11/1996 | Rosenberg et al. ......... 345/179 |
| 5,587,937 A | 12/1996 | Massie et al. .............. 364/578 |
| 5,589,828 A | 12/1996 | Armstrong ................... 341/20 |
| 5,589,854 A | 12/1996 | Tsai ........................... 345/161 |
| 5,591,082 A | 1/1997 | Jensen et al. ................. 463/38 |
| 5,591,924 A | 1/1997 | Hilton |
| 5,623,582 A | 4/1997 | Rosenberg ................... 395/99 |
| 5,629,594 A | 5/1997 | Jacobus et al. ........ 318/568.11 |
| 5,642,469 A | 6/1997 | Hannaford et al. ........... 395/99 |
| 5,643,087 A | 7/1997 | Marcus et al. ............... 463/38 |
| 5,666,138 A | 9/1997 | Culver ....................... 345/161 |
| 5,690,582 A | 11/1997 | Ulrich et al. |
| 5,696,537 A | 12/1997 | Solhjell ...................... 345/164 |
| 5,701,140 A | 12/1997 | Rosenberg et al. |
| 5,709,219 A | 1/1998 | Chen et al. ................. 128/782 |
| 5,721,566 A | 2/1998 | Rosenberg et al. ......... 345/161 |
| 5,724,068 A | 3/1998 | Sanchez et al. ............. 345/161 |
| 5,731,804 A | 3/1998 | Rosenberg .................. 345/156 |
| 5,734,373 A | 3/1998 | Rosenberg et al. ......... 345/161 |
| 5,739,811 A | 4/1998 | Rosenberg et al. ......... 345/161 |
| 5,742,278 A | 4/1998 | Chen et al. ................. 345/156 |
| 5,766,016 A | 6/1998 | Sinclair et al. |
| 5,767,839 A | 6/1998 | Rosenberg |
| 5,769,640 A | 6/1998 | Jacobus et al. ............. 434/262 |
| 5,781,172 A | 7/1998 | Engel et al. ................. 345/164 |
| 5,785,630 A | 7/1998 | Bobick et al. |
| 5,790,108 A | 8/1998 | Salcudean et al. .......... 345/184 |
| 5,802,353 A | 9/1998 | Avila et al. ................. 395/500 |
| 5,816,105 A | 10/1998 | Adelstein ............... 74/471 XY |
| 5,816,823 A | 10/1998 | Naimark et al. ........ 434/307 R |
| 5,821,920 A | 10/1998 | Rosenberg et al. ......... 345/156 |
| 5,872,438 A | 2/1999 | Roston .................. 318/568.11 |
| 5,880,714 A | 3/1999 | Rosenberg et al. ......... 345/156 |
| 5,889,670 A | 3/1999 | Schuler et al. ............. 364/186 |
| 5,889,672 A | 3/1999 | Schuler et al. ............. 364/188 |
| 5,944,151 A | 8/1999 | Jakobs et al. ............ 188/267.1 |
| 5,990,869 A | 11/1999 | Kubica et al. .............. 345/163 |
| 6,037,927 A | 3/2000 | Rosenberg .................. 345/156 |
| 6,057,828 A | 5/2000 | Rosenberg et al. ......... 345/156 |
| 6,111,577 A | 8/2000 | Zilles et al. |
| 6,160,489 A | 12/2000 | Perry et al. |
| 6,201,533 B1 | 3/2001 | Rosenberg et al. ......... 345/156 |
| 6,422,941 B1 | 7/2002 | Thorner et al. |

FOREIGN PATENT DOCUMENTS

| | | |
|---|---|---|
| JP | 4-34610 | 2/1992 |
| JP | H5-192449 | 8/1993 |
| JP | H7-24147 | 1/1995 |
| WO | WO9426167 | 11/1994 |
| WO | WO9502801 | 1/1995 |
| WO | WO9520787 | 8/1995 |
| WO | WO9520788 | 8/1995 |
| WO | WO9520877 | 8/1995 |
| WO | WO9532459 | 11/1995 |
| WO | WO9616397 | 5/1996 |
| WO | WO9622591 | 7/1996 |

OTHER PUBLICATIONS

Russo, Massimo, The Design and Implementation of a Three Degree–of–Freedom Force Output Joystick, 1990.

Kotoku, Tetsuo, A Predictive Display with Force Feedback and its Application to Remote Manipulation Systems with Transmission Time Delay, Jul. 7–10, 1992, Proceedings of the 1992 IEEE/RSJ International Conference on Intelligent Robots and Systems.

Ouh–young, Ming et al., "Using a Manipulator for Force Display in Molecular Docking," IEEE 1988, pp. 1824–1829.

Batter, James J. et al., "Grope–1: A Computer Display to the Sense of Feel," pp. TA–4–188–TA–4–192.

Gotow, J.K., et al., "Perception of Mechanical Properties at the Man–Machine Interface," IEEE 1987, pp. 688–689.

Krueger, Myron W., Artificial Reality 1988, pp. 54–75.

Atkinson, William D. et al, "Computing with Feeling," Comput. & Graphics, vol. 2, No. 2–E, pp. 97–103.

Noll, A. Michael, "Man–Machine Tactile Communication Dissertation," Polytechnic Institute of Brooklyn, Jun. 1971, pp. 1–88.

Ouh–Young, Ming, "Force Display in Molecular Docking," Chapel Hill 1990, pp. 1–85.

Minsky, Margaret et al., "Feeling and Seeing: Issues in Force Display," ACM 1990, pp. 235–242.

Wiker, Steve F. et al., "Development of Tactile Mice for Blind Access to Computers: Importance of Stimulation Locus, Object Size, and Vibrotactile Display Resolution," Proceedings of the Human Factors Society 35th Annual Meeting 1991, pp. 708–712.

Herndon, J.N. et al., "The State–of–the–Art Model M–2 Maintenance System," Proceedings of the 1984 National Topical Meeting on Robotics and Remote Handling in Hostile Environments, pp. 59–65.

Kim, Won S. et al., A Teleoperation Training Simulator with Visual and Kinesthetic Force Virtual Reality.

Fischer, Patrick et al., "Specification and Design of Input Devices for Teleoperation,".

Jacobsen, S.C. et al., "High Performance, High Dexterity, Force Reflective Teleoperator II," ANS Topical Meeting on Robotics & Remote Systems, Albuquerque, New Mexico Feb. 24–27, 1991, pp. 1–10.

Kotoku, Tetsuo et al., "Environment Modeling for the Interactive Display (EMID) Used in Telerobotic Systems," IEEE Nov. 3–5, 1991, pp. 99–1004.

Bejczy, Antal K., "The Phantom Robot: Predictive Displays for Teleoperation with Time Delay," IEEE 1990, pp. 546–550.

Buttolo, Pietro et al., "Pen–Based Force Display for Precision Manipulation in Virtual Environments," IEEE Mar. 1995, pp. 1–8.

Tan, Hong Z. et al., "Human Factors for the Design of Force–Reflecting Haptic Interfaces," Tan, Srinivasan, Eberman, & Chang, ASME WAM 1994, pp. 1–11.

Ellis, R.E. et al., "Design and Evalusation of a High–Performance Prototype Planar Haptic Interface," AMSE Dec. 3, 1993, DSC–vol. 49, pp. 55–64.

Adelstein Bernard D. et al., "A High Performance Two Degree–Freedom Kinesthetic Interface," Massachusetts Institute of Technology 1992, pp. 108–112.

Colgate J. Edward et al., Implementation of Stiff Virtual Walls in Force–Reflecting Interfaces, Sep. 22, 1993.

Iwata, Hiroo et al, Volume Haptization, IEEE 1993, pp. 16–18.

Fischer, Patrick et al., "Specification and Design of Input Devices for Teleoperation," 1990.

Rosenberg, Louis B., "The Use of Virtual Fixtures to Enhance Operator Performance in Time Delayed Teleoperation," Crew Systems Directorate, Wright–Patterson, Air Force Material Command, Mar. 1993, pp. 1–45.

Rosenberg, Louis B., "Perceptual Design of a Virtual Rigid Surface Contact," Center for Design Research Standford University, Air Force Material Command, Apr. 1993, pp. 1–41.

Rosenberg, Louis B., et al., "Perceptual Decomposition of Virtual Haptic Surfaces," IEEE, Oct. 1993.

Fisher, S.S. et al., "Virtual Environment Display System," ACM 1986 Workshop on Interactive 3D Graphics, Oct. 1986.

Tavkhelidze, D.S. et al., "Kinematic Analysis of Five–Link Spherical Mechanisms," Mechanism and Machine Theory, Pergamon Press, 1974, vol. 9, pp. 181–190.

Rosenberg, Louis B., "Virtual Fixtures as Tools to Enhance Operator Performance in Telepresence Environments," SPIE Telemanipulator Technology, 1993.

Rosenberg, Louis B., "Virtual Haptic Overlays Enhance Performance in Telepresence Tasks," SPIE 1994.

Burdea, Grigore et al., "Dextrous Telerobotics with Force Feedback–An Overview," Robotica 1991, vol. 9.

Colgate, J. Edward et al., "Implementation of Stiff Virtual Walls in Force–Reflecting Interfaces," 1993, pp. 1–9.

Yamakita, M. et al., Tele–Virtual Reality of Dynamic Mechanical Model, IEEE Jul. 7–10, 1992, pp. 1103–1110.

Adlestein, Bernard D. et al., "Design and Implementation of a Force Reflecting Manipulandum for Manual Control Research," 1992, pp. 1–24.

Ouh–young, Ming et al., "Force Display Performs Better than Visual Display in a Simple 6–D Docking Task," IEEE 1989, pp. 1462–1466.

Kim, Won S. et al., "Graphics Displays for Operator Aid in Telemanipulation," IEEE 1991, pp. 1059–1067.

Hannaford, Blake et al., "Performance Evaluation of a Six–Axis Generalized Force–Reflecting Teleoperator," IEEE May/Jun. 1991, vol. 21, No. 3, pp. 620–633.

Kilpatrick, P., "The Use of a Kinesthetic Supplement in an Interactive Graphics System," University of North Carolina, 1976, pp. 1–176.

Winey III, C., "Computer Simulated Visual and Tactile Feedback as an Aid to Manipulator and Vehicle Control," Dept. of Mech. Engineering, MIT, 1981, pp. 1–79.

Kelley, A.J. et al., "On the Development of a Force–feedback Mouse and its Integration into a Graphical User Interface," Symp. on Haptic Interfaces for Virtual Environment and Teleoperator Systems, 1993 Int'l Mech. Engineering Congress and Exhibition, 1994, pp. 1–8.

Iwata, H., "Pen–based Haptic Virtual Environment," IEEE 0–7803–1363–1, 1993, pp. 287–292.

Hirota, K. et al., "Development of Surface Display," IEEE 0–7803–1363–1, 1993, pp. 256–262.

Iwata, H., "Artificial Reality with Force–Feedback: Development of Desktop Virtual Space with Compact Master Manipulator," Computer Graphics, vol. 24, No. 4, 1990, pp. 165–170.

Kelley, A.J. et al., "MagicMouse: Tactile and Kinesthetic Feedback in the Human–Computer Interface using an Electromagnetically Actuated Input/Output Device," Dept. of Elec. Engineering, Univ. of British Columbia, 1993, pp. 1–27.

Howe et al., "Task Performance with a Dextrous Teleoperated Hand System," Proc. of SPIE, vol. 1833, 1992, pp. 1–9.

Bostrom, M. et al., "Design of An Interactive Lumbar Puncture Simulator with Tactile Feedback," IEEE 0–7803–1363–1, 1993, pp. 280–286.

Millman, P. et al., "Design of a Four Degree–of–Freedom Force Reflecting Manipulandum with a Specified Force/torque Workspace," IEEE CH2969–4/91, 1991, pp. 1488–1492.

Brooks, Jr., F. et al., "Project GROPE–Haptic Displays for Scientific Visualization," Computer Graphics, vol. 24, No. 4, 1990, pp. 177–185.

Hannaford, B. et al., "Force–Feedback Cursor Control," NASA Tech Brief, vol. 13, No. 11, Item #21, 1989, pp. 1–4.

Ouh–young, M. et al., "Creating an Illusion of Feel: Control Issues in Force Display," Univ. of North Carolina, Computer Science Dept., 1989, pp. 1–14.

Ramstein, C. et al., "The Pantograph: A Large Workspace Haptic Device for Multimodal Human–Computer Interaction," Computer–Human Interaction, CHI '94, 1994, pp. 1–3.

Hayward, V. et al., "Design and Multi–Objective Optimization of a Linkage for a Haptic Interface," Advances in Robot Kinematics and Computationed Geometry, Kluwer Academic Publishers, 1994, pp. 359–368.

Corrao, J.M., "Control Loading," American Institute of Aeronautics and Astronautic's Flight Simulation Update 1988, Jan. 11–15, 1988.

Hasser, C., "Force–Reflecting Anthropomorphic Hand Masters," AL/CF–TR–1995–0110, 1995, pp. 5–117.

Baigrie, "Electric Control Loading—A Low Cost, High Performance Alternative," *Proceedings of Interservice/Industry Training Systems Conference*, pp. 247–254, Nov. 6–8, 1990.

Iwata, "Pen–based Haptic Virtual Environment," 0–7803–1363–1/93 IEEE, pp. 287–292, 1993.

Russo, "The Design and Implementation of a Three Degree of Freedom Force Output Joystick," *MIT Libraries Archives* pp. 1–131, May 1990, archived Aug. 14, 1990.

Brooks et al., "Hand Controllers for Teleoperation—A State–of–the–Art Technology Survey and Evaluation," *JPL Publication 85–11*, NASA–CR–175890; N85–28559, pp. 1–84, Mar. 1, 1985.

Jones et al., "A perceptual analysis of stiffness," ISSN 0014–4819 Springer International (Springer–Verlag); *Experimental Brain Research*, vol. 79, No. 1, pp. 150–156, 1990.

Burdea et al., "Distributed Virtual Force Feedback, Lecture Notes for Workshop on Force Display in Virtual Environments and its Application to Robotic Teleoperation," *1993 IEEE International Conference on Robotics and Automation*, pp. 25–44, May 02, 1993.

Snow et al., Model–X Force–Reflecting–Hand–Controller, NT Control No. NPO–17851; JPL Case No. 7348, pp. 1–4 with 45 pages of attachments, Jun. 15, 1989.

Ouh–Young, "Force Display in Molecular Docking," Doctoral Dissertation, University of North Carolina at Chapel Hill, UMI Order No. 9034744, p. 1–369, 1990.

Tadros, "Control System Design for a Three Degree of Freedom Virtual Environment Simulator Using Motor/Brake Pair Actuators," *MIT Archive*, pp. 1–88, Feb. 1990, archived Aug. 13, 1990.

Caldwell et al., "Enhanced Tactile Feedback (Tele–Taction) Using a Multi–Functional Sensory System," 1050–4729/93, pp. 955–960, 1993.

Adelstein et al., "Design and Implementation of a Force Reflecting Manipulandum for Manual Control research," DSC–vol. 42, *Advances in Robotics*, pp. 1–12, 1992.

Gotow et al., "Controlled Impedance Test Apparatus for Studying Human Interpretation of Kinesthetic Feedback," WA11–11:00, pp. 332–337.

Stanley et al., "Computer Simulation of Interacting Dynamic Mechanical Systems Using Distributed Memory Parallel Processors," DSC–vol. 42, *Advances in Robotics*, pp. 55–61, ASME 1992.

Russo, "Controlling Dissipative Magnetic Particle Brakes in Force Reflective Devices," DSC–vol. 42, *Advances in Robotics*, pp. 63–70, ASME 1992.

Kontarinis et al., "Display of High–Frequency Tactile Information to Teleoperators," *Telemanipulator Technology and Space Telerobotics*, Won S. Kim, Editor, Proc. SPIE vol. 2057, pp. 40–50, Sep. 7–9, 1993.

Patrick et al., "Design and Testing of A Non–reactive, Fingertip, Tactile Display for Interaction with Remote Environments," *Cooperative Intelligent Robotics in Space*, Rui J. deFigueiredo et al, Editor, Proc. SPIE vol. 1387, pp. 215–222, 1990.

Adelstein, "A Virtual Environment System For The Study of Human Arm Tremor," *Ph.D. Dissertation*, Dept. of Mechanical Engineering, MIT, Jun. 1989, archived Mar. 13, 1990.

Bejczy, "Sensors, Controls, and Man–Machine Interface for Advanced Teleoperation," *Science*, vol. 208, No. 4450, pp. 1327–1335, 1980.

Bejczy et al., "Generalization of Bilateral Force–Reflecting Control of Manipulators," *Proceedings Of Fourth CISM–IFToMM*, Sep. 8–12, 1981.

McAffee et al., "Teleoperator Subsystem/Telerobot Demonstrator: Force Reflecting Hand Controller Equipment Manual," *JPL* 1988, JPL D–5172.

Minsky, "Computational Hapties: The Sandpaper System for Synthesizing Texture for a Force–Feedback Display," *Ph.D. Dissertation*, MIT, Jun. 1995, archived Jul. 6, 1995.

Jacobsen et al., "High Performance, Dextrous Telerobotic Manipulator With Force Reflection," *Intervention/ROV '91 Conference & Exposition*, Hollywood, Florida, May 21–23, 1991.

Shimoga, "Finger Force and Touch Feedback Issues in Dexterous Telemanipulation," *Proceedings of Fourth Annual Conference on Intelligent Robotic Systems for Space Exploration*, Rensselaer Polytechnic Institute, Sep. 30–Oct. 1, 1992.

IBM Technical Disclosure Bulletin, "Mouse Ball–Actuating Device With Force and Tactile Feedback," vol. 32, No. 9B, Feb. 1990.

Terry et al., "Tactile Feedback In A Computer Mouse," *Proceedings of Fourteenth Annual Northeast Bioengineering Conference, University of New Hampshire*, Mar. 10–11, 1988.

Howe, "A Force–Reflecting Teleoperated Hand System for the Study of Tactile Sensing in Precision Manipulation," *Proceedings of the 1992 IEEE International Conference on Robotics and Automation*, Nice, France, May 1992.

Eberhardt et al., "OMAR—A Haptic display for speech perception by deaf and deaf–blind individuals," *IEEE Virtual Reality Annual International Symposium*, Seattle, WA, Sep. 18–22, 1993.

Rabinowitz et al., "Multidimensional tactile displays: Identification of vibratory intensity, frequency, and contractor area," *Journal of the Acoustical Society of America*, vol. 82, No. 4, Oct. 1987.

Bejcy et al., "Kinesthetic Coupling Between Operator and Remote Manipulator," *International Computer Technology Conference, The American Society of Mechanical Engineers*, San Francisco, CA, Aug. 12–15, 1980.

Bejczy et al., "A Laboratory Breadboard System For Dual–Arm Teleoperation," *SOAR '89 Workshop, JSC*, Houston, TX, Jul. 25–27, 1989.

Ouhyoung et al., "A Low–Cost Force Feedback Joystick and Its Use in PC Video Games," *IEEE Transactions on Consumer Electronics*, vol. 41, No. 3, Aug. 1995.

Marcus, "Touch Feedback in Surgery," *Proceedings of Virtual Reality and Medicine The Cutting Edge*, Sep. 8–11, 1994.

Bejczy, et al., "Universal Computer Control System (UCCS) For Space Telerobots," CH2413–3/87/0000/0318501.00 1987 IEEE, 1987.

Wiker, "Teletouch Display Development: Phase 1 Report," *Technical Report 1230*, Naval Ocean Systems Center, San Diego, Jul. 1988.

Rosenberg, "Virtual Fixtures: Perceptual Overlays Enhance Operator Performance In Telepresence Tasks," *Ph.D. Dissertation*, Stanford University, Jun. 1994.

Meyer, Kenneth et al., "Survey of Position Tracker," The Massachusetts Institute of Technology, Spring 1992, vol. 1, No. 2, pp. 173–200.

"3D Human Interface Tool," 1994 Immersion Human Interface Corporation.

"The Personal Digitizer," 1994 Immersion Human Interface Corporation.

Kim, Won S. et al., "A Teleoperation Training Simulator with Visual and Kinesthetic Force Virtual Reality", Human Vision, Visual Proceedings, Proc. SPIE 1666, San Jose, CA, Feb. 1992.

"Proceedings of the IFIP Congress 65," International Federation for Information Processing, Information Processing 1965, vol. 3, New York, May 24–29, 1965, p. 506.

"High Performance Model of the Immersion Probe," Immersion Probe–MD.TM, Immersion Corporation; date unknown.

"Call it Palpable Progress," Science & Technology, Business Week, Oct. 9, 1995, p. 93.

"Useful Technology for Your Idea File," Design News, Mar. 7, 1994, p. 63.

Rosenberg, Louis b., "The Use of Virtual Fixtures as Perceptual Overlays to Enhance Operator Performance in Remote Environments," Air Force Material Command, Sep. 1992, pp. 1–42.

Smith, Geoffrey, "Call it Palpable Progress," Business Week, Oct. 9, 1995, pp. 95–96.

Aukstakalnis et al., "Silicon MIrage: The Art and Science of Virtual Reality," ISBN 0–938151–82–7, pp. 129–180, 1992.

Bliss, "Optical–to–Tactile Image Conversion for the Blind," IEEE Transactions on Man–Machine Systems, vol. MMS–11, No. 1, pp. 58–65, Mar. 1970.

Calder, "Design of A Force–Feedback Touch–Introducing Actuator For Teleoperator Robot Control," Bachelor of Science Thesis, MIT, Jun. 23, 1993.

"Cyberman Technical Specification," Logitech Cyberman SWIFT Supplement, Apr. 5, 1994.

Eberhardt et al., "Inducing Dynamic Haptic Perception by The Hand: System Description and Some Results," DSC–vol. 55–1, Dynamic Systems and Control: vol. 1, ASME 1994, pp. 345–351.

Gobel et al., "Tactile Feedback Applied to Computer Mice," International Journal of Human–Computer Interaction, vol. 7, No. 1, pp. 1–24, 1995.

Johnson, "Shape–Memory Alloy Tactile Feedback Actuator," Armstrong Aerospace Medical Research Laboratory, AAMRL–TR–90–039, Aug. 1990.

Kaczmarek et al., "Tactile Displays," Virtual Environment Technologies, pp. 349–414.

Kontarinis et al., "Tactile Display of Vibratory Information in Teleoperation and Virtual Environments," Presence, vol. 4, No. 4, pp. 387–402, 1995.

Lake, "Cyberman from Logitech," Gamebytes, 1994.

Noll, "Man–Machine Tactile," SID Journal, Jul./Aug. 1972 Issue.

Ouhyoung et al., "The Development of A Low–Cost Force Feedback Joystick and Its Use in the Virtual Reality Environment," Proceedings of the Third Pacific Conference on Computer Graphics and Applications, Pacific Graphics '95, Seoul Korea, Aug. 21–24, 1995, pp. 309–319.

Pimentel et al., "Virtual Reality: through the new looking glass," $2^{nd}$ Edition; McGraw–Hill, ISBN 0–07–050167–X, pp. 41–202, 1994.

Patrick, "Design, Construction, and Testing of a Fingertip Tactile Display for Interaction with Virtual and Remote Environments," Master of Science Thesis, MIT, Nov. 8, 1990.

"Component Maintenance Manual With Illustrated Parts, List, Coaxial Control Shaker Part No. C–25502," Safe Flight Instrument Corporation, revised Jan. 28, 2002 (3 pages).

"Technical Manual Overhaul Instructions With Parts Breakdown, Coaxial Control Shaker Part No. C–25502," Safe Flight Instrument Corporation, Revised Jul. 15, 1980 (23 pages).

Scannell, "Taking a Joystick Ride," Computer Currents, Boston Edition, vol. 9, No. 11, Nov. 1994.

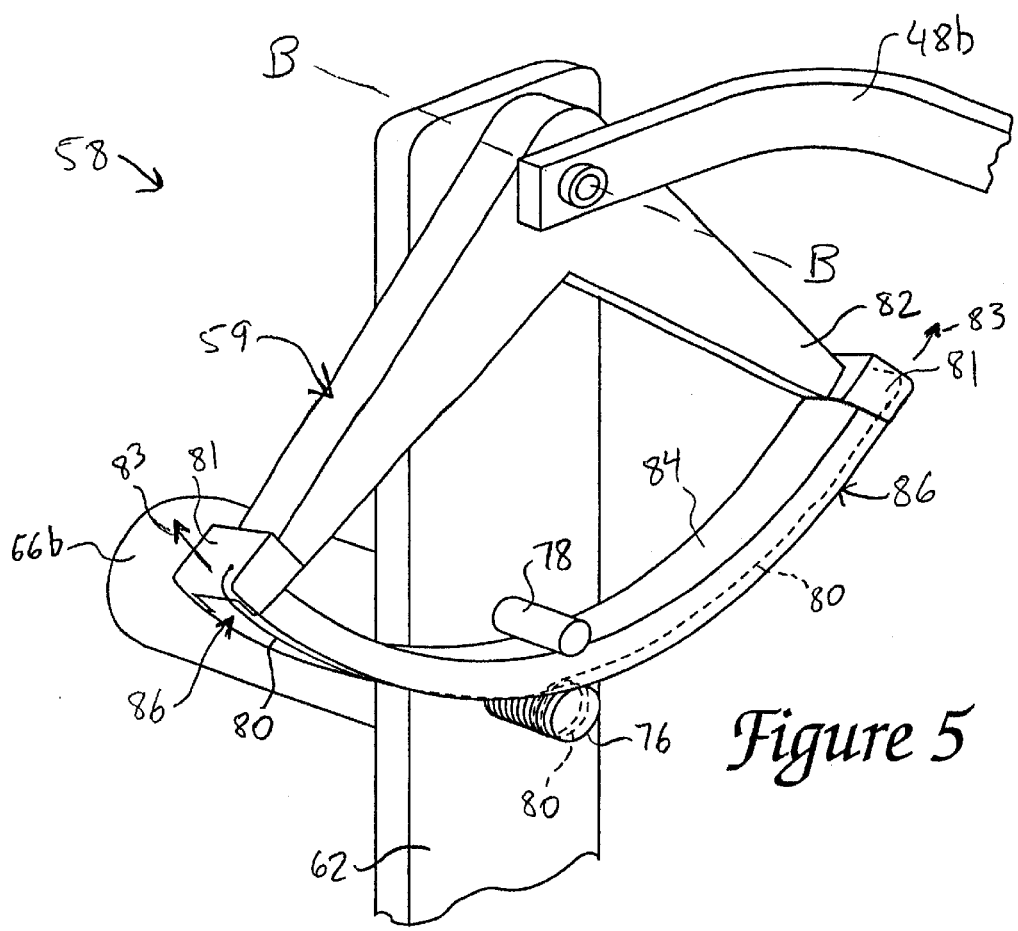
*Figure 5*
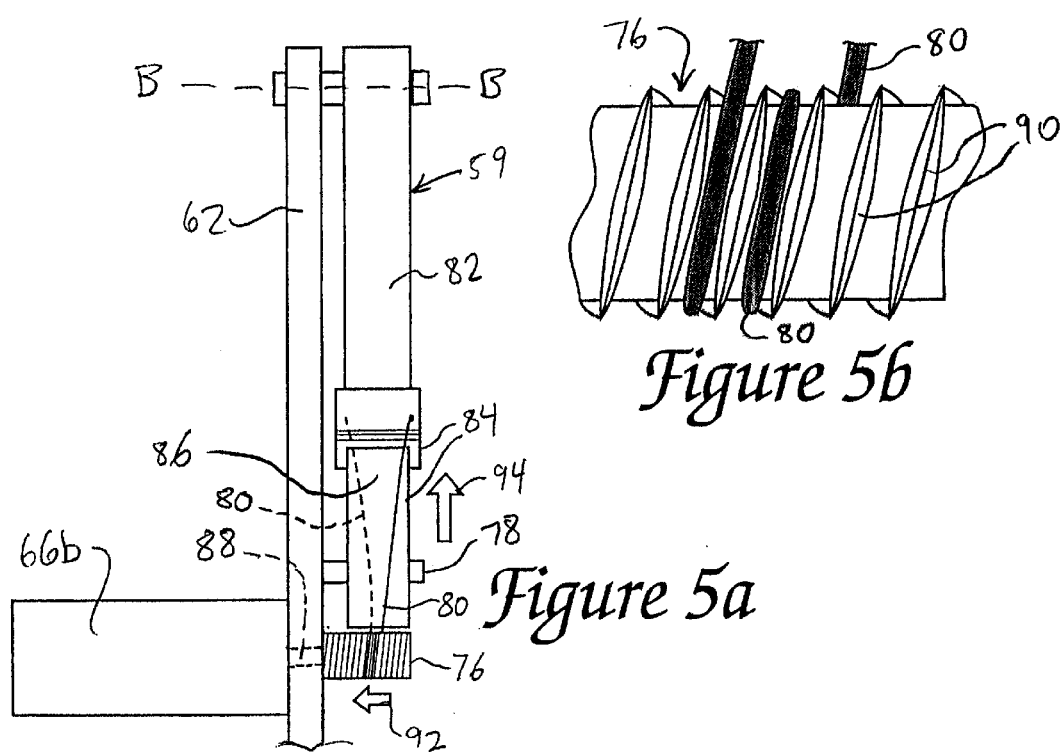
*Figure 5b*
*Figure 5a*

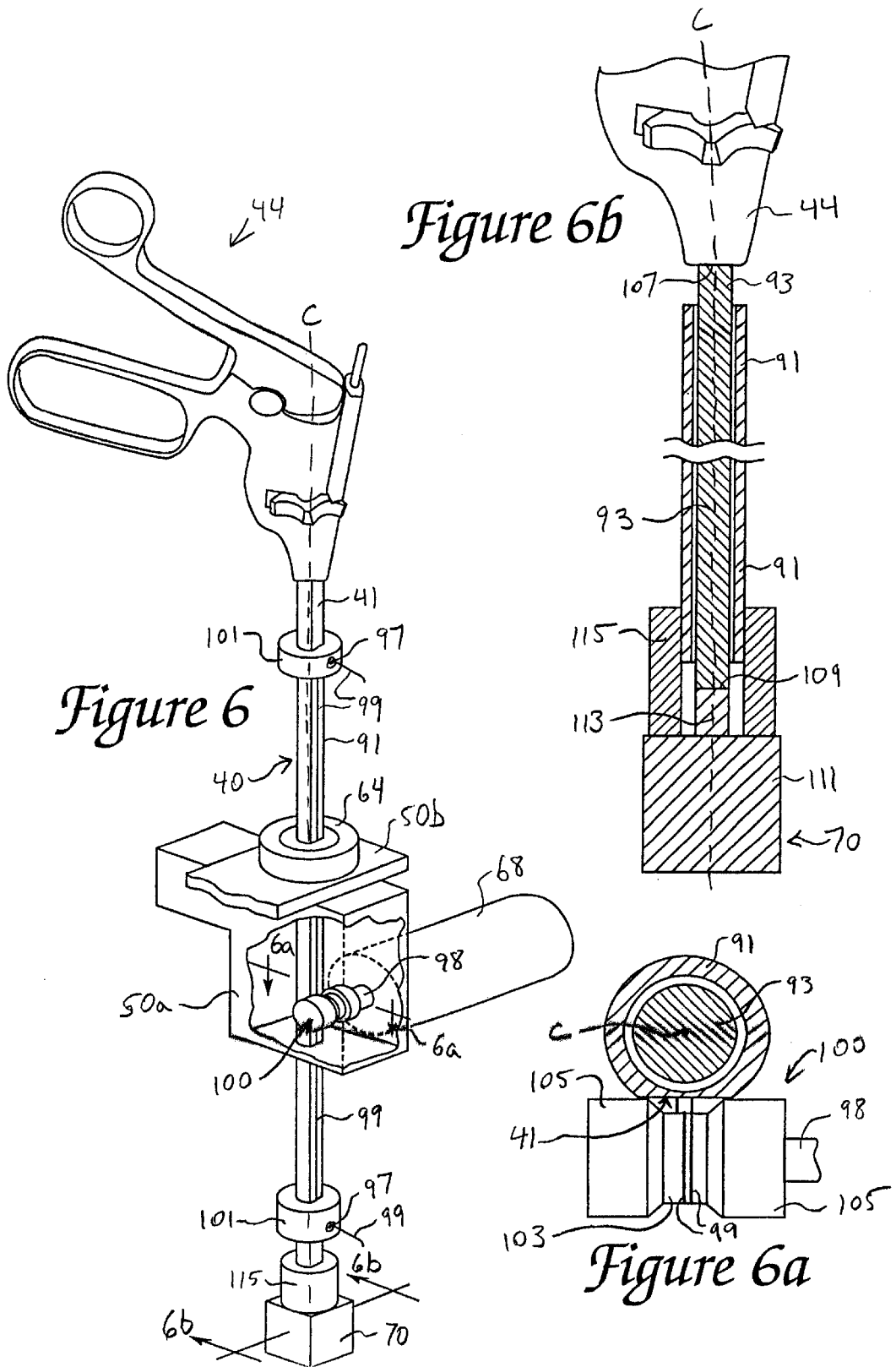

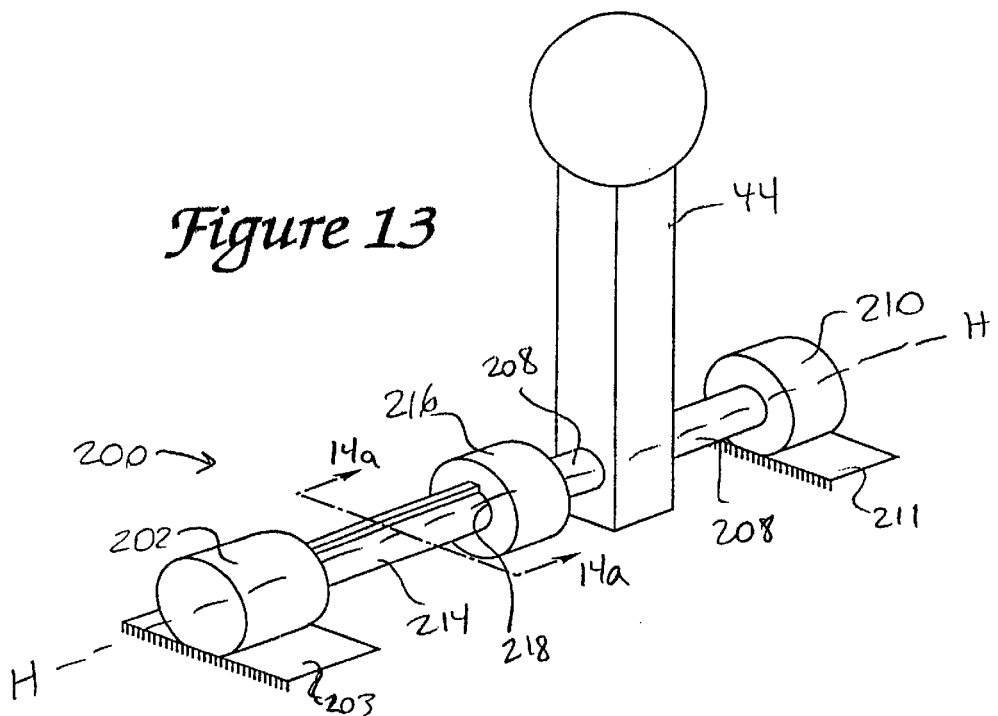
*Figure 13*
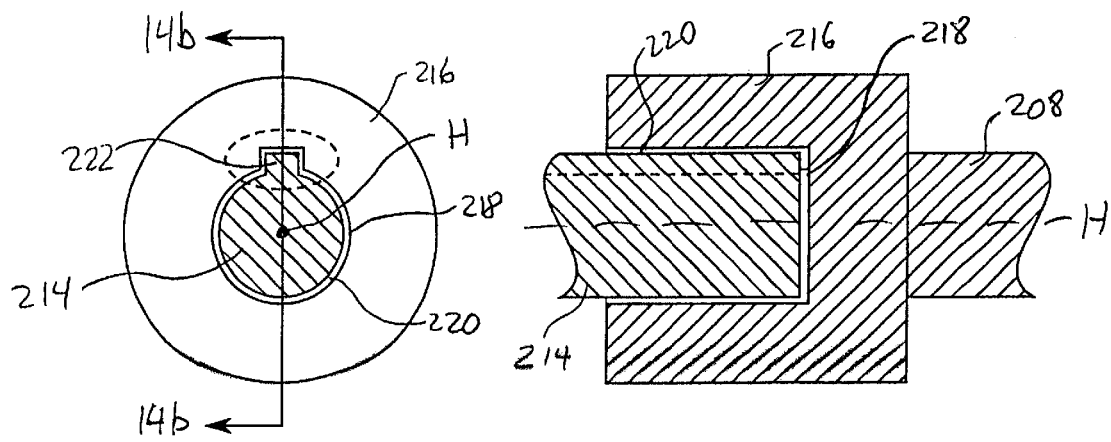
*Figure 14a*  *Figure 14b*
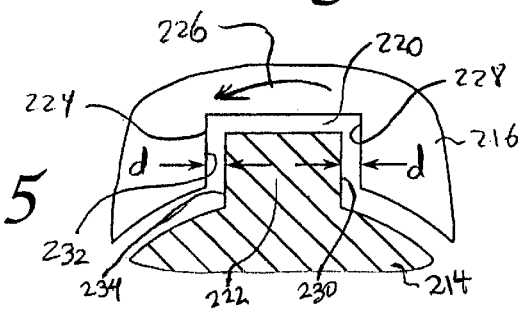
*Figure 15*

PASSIVE FORCE FEEDBACK FOR COMPUTER INTERFACE DEVICES

CROSS REFERENCE TO RELATED APPLICATIONS

This application is a continuation of patent application Ser. No. 08/932,316, filed on Sep. 17, 1997, now U.S. Pat. No. 6,154,198, which is a continuation of patent application Ser. No. 08/400,233, filed on Mar. 3, 1995, now U.S. Pat. No. 5,767,839, which is a CIP of patent application Ser. No. 08/374,288, filed on Jan. 18, 1995, now U.S. Pat. No. 5,731,804.

BACKGROUND OF THE INVENTION

The present invention relates generally to interface devices between humans and computers, and more particularly to computer input devices that provide force feedback to the user.

Virtual reality computer systems provide users with the illusion that they are part of a "virtual" environment. A virtual reality system will typically include a computer processor, such as a personal computer or workstation, specialized virtual reality software, and virtual reality I/O devices such as head mounted displays, sensor gloves, three dimensional ("3D") pointers, etc.

One common use for virtual reality computer systems is for training. In many fields, such as aviation and vehicle and systems operation, virtual reality systems have been used successfully to allow a user to learn from and experience a realistic "virtual" environment. The appeal of using virtual reality computer systems for training relates, in part, to the ability of such systems to allow trainees the luxury of confidently operating in a highly realistic environment and making mistakes without "real world" consequences. Thus, for example, a trainee pilot or automobile driver can learn to operate a vehicle using a virtual reality simulator without concern for accidents that would cause injury, death and/or property damage in the real world. Similarly, operators of complex systems, e.g., nuclear power plants and weapons systems, can safely practice a wide variety of training scenarios that would risk life or property if performed in reality.

For example, a virtual reality computer system can allow a doctor-trainee or other human operator or user to "manipulate" a scalpel or probe within a computer-simulated "body", and thereby perform medical procedures on a virtual patient. In this instance, the I/O device which is typically a 3D pointer, stylus, or the like is used to represent a surgical instrument such as a scalpel or probe. As the "scalpel" or "probe" moves within a provided space or structure, results of such movement are updated and displayed in a body image displayed on the screen of the computer system so that the operator can gain the experience of performing such a procedure without practicing on an actual human being or a cadaver.

In other applications, virtual reality computer systems allow a user to handle and manipulate the controls of complicated and expensive vehicles and machinery. For example, a pilot or astronaut in training can operate a fighter aircraft or spacecraft by manipulating controls such as a control joystick and other buttons and view the results of controlling the aircraft on a virtual reality simulation of the aircraft in flight. In yet other applications, a user can manipulate objects and tools in the real world, such as a stylus, and view the results of the manipulation in a virtual reality world with a "virtual stylus" viewed on a screen, in 3-D goggles, etc.

For virtual reality systems to provide a realistic (and therefore effective) experience for the user, sensory feedback and manual interaction should be as natural as possible. As virtual reality systems become more powerful and as the number of potential applications increases, there is a growing need for specific human/computer interface devices which allow users to interface with computer simulations with tools that realistically emulate the activities being represented within the virtual simulation. Such procedures as laparoscopic surgery, catheter insertion, and epidural analgesia should be realistically simulated with suitable human/computer interface devices if the doctor is to be properly trained. Similarly, a user should be provided with a realistic interface for manipulating controls or objects in a virtual reality simulation to gain useful experience.

While the state of the air in virtual simulation and medical imaging provides a rich and realistic visual feedback, there is a great need for new human/computer interface tools which allow users to perform natural manual interactions with the computer simulation. For medical simulation, there is a strong need to provide doctors with a realistic mechanism for performing the manual activities associated with medical procedures while allowing a computer to accurately keep truck of their actions. There is also a need in other simulations to provide virtual reality users with accurate and natural interfaces for their particular tasks.

In addition to sensing and tracking a user's manual activity and feeding such information to the controlling computer to provide a 3D visual representation to the user, a human interface mechanism should also provide force or tactile ("haptic") feedback to the user. The need for the user to obtain realistic tactile information and experience tactile sensation is extensive in many kinds of simulation. For example, in medical/surgical simulations, the "feel" of a probe or scalpel simulator is important as the probe is moved within the simulated body. It would be invaluable to a medical trainee to learn how an instrument moves within a body, how much force is required depending on the operation performed, the space available in a body to manipulate an instrument, etc. In simulations of vehicles or equipment, force feedback for controls such as a joystick can be necessary to realistically teach a user the force required to move the joystick when steering in specific situations, such as in a high acceleration environment of an aircraft. In virtual world simulations where the user can manipulate objects, force feedback is necessary to realistically simulate physical objects; for example, if a user touches a pen to a table, the user should feel the impact of the pen on the table. An effective human interface not only acts as an input device for tracking motion, but also as an output device for producing realistic tactile sensations. A "high bandwidth" interface system, which is an interface that accurately responds to signals having fast changes and a broad range of frequencies as well as providing such signals accurately to a control system, is therefore desirable in these and other applications.

There are number of devices that are commercially available for interfacing a human with a computer for virtual reality simulations. There are, for example, 2-dimensional input devices such as mice, trackballs, and digitizing tablets. However, 2-dimensional input devices tend to be awkward and inadequate to the task of interfacing with 3-dimensional virtual reality simulations.

Other 3-dimensional interface devices are available. A 3-dimensional human/computer interface tool sold under the trademark Immersion PROBE™ is marketed by Immersion Human Interface Corporation of Santa Clara, Calif., and allows manual control in 3-dimensional virtual reality computer environments. A pen-like stylus allows for dexterous 3-dimensional manipulation, and the position and orientation of the stylus is communicated to a host computer. The Immersion PROBE has six degrees of freedom which convey spatial coordinates (x, y, z) and orientation (roll, pitch, yaw) of the stylus to the host computer.

While the Immersion PROBE is an excellent 3-dimensional interface tool, it may be inappropriate for certain virtual reality simulation applications. For example, in some of the aforementioned medical simulations three or four degrees of freedom of a 3-dimensional human/computer interface tool is sufficient and, often, more desirable than five or six degrees of freedom because it more accurately mimics the real-life constraints of the actual medical procedure. More importantly, the Immersion PROBE does not provide force feedback to a user and thus does not allow a user to experience an entire sensory dimension in virtual reality simulations.

In typical multi-degree of freedom apparatuses that include force feedback, there are several disadvantages. Since actuators which supply force feedback tend to be heavier and larger than sensors, they would provide inertial constraints if added to a device such as the Immersion PROBE. There is also the problem of coupled actuators. In a typical force feedback device, a serial chain of links and actuators is implemented to achieve multiple degrees of freedom in a desired object positioned at the end of the chain, i.e., each actuator is coupled to the previous actuator. The user who manipulates the object must carry the inertia of all of the subsequent actuators and links except for the first actuator in the chain, which is grounded. While it is possible to ground all of the actuators in a serial chain by using a complex transmission of cables or belts, the end result is a low stiffness, high friction, high damping transmission which corrupts the bandwidth of the system, providing the user with an unresponsive and inaccurate interface. These types of interfaces also introduce tactile "noise" to the user through fraction and compliance in signal transmission and limit the degree of sensitivity conveyed to the user through the actuators of the device.

Other existing devices provide force feedback to a user. In U.S. Pat. No. 5,184,319, by J. Kramer, an interface is described which provides force and texture information to a user of a computer system. The interface consists of an glove or "exoskeleton" which is worn over the user's appendages, such as fingers, arms, or body. Forces can be applied to the user's appendages using tendon assemblies and actuators controlled by a computer system to simulate force and textual feedback. However, the system described by Kramer is not easily applicable to simulation environments such as those mentioned above where an object is referenced in 3D space and force feedback is applied to the object. The forces applied to the user in Kramer are with reference to the body of the user, the absolute location of the user's appendages are not easily calculated. In addition, the exoskeleton devices of Kramer can be cumbersome or even dangerous to the user if extensive devices are worn over the user's appendages. Furthermore, the devices disclosed in Kramer are complex mechanisms in which many actuators must be used to provide force feedback to the user.

In other situations, low-cost and portable mechanical interfaces having force feedback are desirable. Active actuators, such as motors, generate forces on an interface device and the user manipulating the interface device so that the interface device can move independently of the user. While active actuators often provide quite realistic force feedback, they can also be quite bulky and typically require large power supplies to operate. In addition, active actuators typically require high speed control signals to operate effectively and provide stability. In many situations, such high speed control signals and high power drive signals are not available or too costly, especially in the competitive, low-cost market of personal computers. Furthermore, active actuators can sometimes prove unsafe for a user when strong, unexpected forces are generated on a user of the interface who does not expect those forces.

Therefore, a less complex, more compact, and less expensive alternative to a human/computer interface tool having force feedback, lower inertia, higher bandwidth, and less noise is desirable for certain applications. A less expensive interface requiring slower communication signals and being safer for the user is also needed.

SUMMARY OF THE INVENTION

The present invention provides a human/computer interface apparatus and method which can provide from one to six degrees of freedom and highly realistic force feedback to a user of the apparatus. The preferred apparatus includes a transducer system including passive actuators that require lower power and slower control signals than active actuators. A desired amount of play, such as compliance or backlash, is preferably introduced in the system to allow a computer system to effectively control an object connected to the interface and transducer system.

An apparatus of the present invention for interfacing the motion of an object with an electrical system includes a sensor, such as a digital encoder, that detects movement of an object along a degree of freedom. The sensor is preferably coupled to the object. The sensor has a sensing resolution, and preferably an amount of play less than the sensing resolution exists between the sensor and the object. More preferably, an amount of play that is an order of magnitide less than the sensing resolution, or a negligible amount of play, exists between the sensor and object.

The apparatus also includes an actuator assembly that includes an actuator coupled to the object to transmit a force to the object along the degree of freedom. The actuator is preferably an electromechanical passive resistance element, such as a magnetic particle brake. The actuator assembly also includes a play mechanism that is coupled to the actuator for providing a desired amount of play between the actuator and the object along the degree of freedom. The desired amount of play is greater than the sensing resolution of the sensor so that the sensor can detect the play. Such desired play can include torsion flex (compliance) or rotary backlash. When the play is provided as rotary backlash, the actuator is preferably coupled to a coupling having a keyed bore which is smaller than a keyed shaft that is received by the keyed bore. The actuator and the sensor provide an electromechanical interface between the object and the electrical system.

Another apparatus for interfacing the motion of an object with an electrical system in accordance with the present invention includes a gimbal mechanism providing a first revolute degree of freedom to an object engaged with the gimbal mechanism about an axis of rotation. The gimbal mechanism preferably includes a closed loop five member linkage. A sensor is rigidly coupled to the gimbal mechanism for sensing positions of the object along the first degree of freedom, where the sensor has a sensing resolution. A braking mechanism is coupled to the gimbal mechanism to create a drag along the first degree of freedom and provides a desired amount of play between the actuator and the object along the degree of freedom. The desired amount of play is equal to or greater than the sensing resolution of the sensor. The actuator and the sensor provide an electromechanical interface between the object and the electrical system.

In the described embodiment, the apparatus further includes a sensor and braking mechanism for sensing and providing force feedback along a second degree of freedom provided by the gimbal mechanism. The braking mechanism includes an actuator and coupling to provide the desired amount of play. A capstan drive mechanism is coupled between the actuator and the gimbal mechanism. The capstan drive mechanism transmits the force generated by the actuator to the gimbal mechanism and transmits forces applied to the gimbal mechanism by a user to the sensor. A linear axis member can also be coupled to the gimbal mechanism at the intersection of the two axes of rotation. The object is coupled to the linear axis member and the linear axis member and object can be translated along a third axis in a third degree of freedom. A third degree of freedom transducer can be used to create a drag along the third degrees of freedom and to sense translation of the linear axis member. Transducers can also be included for sensing positions of said object along fourth, fifth, and sixth degrees of freedom. The object can be a surgical tool, a stylus, a joystick, or similar articles.

A method for interfacing motion of an object with an electrical system includes steps of defining an origin in 3-dimensional space and providing a gimbal mechanism movable relative to the origin such that an object engaged with the gimbal mechanism has a degree of freedom. Positions of the object along the degree of freedom are sensed with a sensor such that play less than the sensing resolution of the sensor is allowed between the sensor and the object. A drag is created from a brake along the degree of freedom, and a desired amount of play greater than or equal to the sensing resolution of the sensor is allowed between the actuator and the object. Output electrical signals from the electrical system are converted into movement of the object and movement of the object is converted into electrical signals input to the electrical system. The play preferably includes rotary backlash and/or torsion flex.

An electromechanical input/output device according to the present invention includes an object capable of moving along at least one degree of freedom. A sensor senses movement along the provided degrees of freedom and provides an electrical signal from this movement. An electromechanical brake mechanism applies a resistive force to the object along said at least one degree of freedom and is responsive to a braking signal, and a play mechanism couples the brake mechanism to the object. The sensor can detect movements of the object along the degree of freedom when the brake mechanism is engaged due to the play mechanism. Preferably, the sensor is coupled to the object and detects rotational movement of the object. The play mechanism includes a coupling rigidly coupled to the object and non-rigidly coupled to the brake mechanism. The object is capable of being moved along the degree of freedom by a user who is grasping the object. A computer system preferably provides the braking signal to the brake mechanism and receives the electrical signal from the sensor.

In yet another embodiment of the present invention, A system for controlling an electromechanical interface apparatus manipulated by a user includes a digital computer system for receiving an input control signal and for providing an output control signal which updates a process in response to the input control signal. A passive actuator for receiving the output control signal provides a resistive force along a degree of freedom to an object coupled to the passive actuator. The object is preferably grasped and moved by the user. The resistance force is based on information in the output control signal and resists a force applied to the object by the user along the degree of freedom. A sensor detects motion of the object and outputs the input control signal including information representative of the position and motion of the object to the digital computer system. Preferably, the digital computer updates a simulation process in response to the input control signal and displays a simulation to the user on a display screen. A play mechanism preferably provides a desired amount of play between the actuator and the object, the desired amount of play being greater than a sensing resolution of the sensor. A serial interface can output the output control signal from the computer system and can receive the input control signal to the computer system. A digital to analog converter can receive the output control signal, convert the output control signal to an analog control signal, and output the analog control signal to the passive actuator. Finally, a microprocessor can provide the output control signal from the serial interface to the digital to analog converter and can receive the input control signal from the sensor.

In another method for controlling an interface apparatus according to the present invention, steps include sensing the current position of an object coupled to an interface apparatus and determining the difference between the current position of the object and a previous position of the object. A magnitude of a resistive force to be applied to the object is determined; this magnitude is based at least in part on the difference between the current position and the previous position. A control signal is provided to a passive actuator to transmit a resistive force having the determined magnitude to the object. The above steps are repeated as the user moves the object. The current position of the object is preferably sensed even when the object is locked into a position by the passive actuator. Preferably, a damping constant is determined which is multiplied by the difference to determine the magnitude of the resistive force. The above steps can be implemented for a plurality of sensor and passive actuator pairs.

The interface of the present invention includes a transducer system having an actuator and a sensor. The actuator is preferably a passive actuator, such as magnetic particle brakes, that require less power and slower control signals than active actuators. A desired amount of play, such as backlash or compliance, is provided between the actuator and an interfaced object so that a controlling computer can determine the direction that a user moves the object, even when the passive actuators are holding the object stationary. In addition, the user preferably cannot feel the play in the system. The transducer system can be used on a variety of mechanical interfaces providing one to six degrees of freedom and can also be used with capstan drive mechanisms so that the desired play is substantially the only play introduced to the interface system. These improvements allow a computer system to have more complete and accurate control over a low-cost interface providing realistic force feedback.

These and other advantages of the present invention will become apparent to those skilled in the art upon a reading of the following specification of the invention and a study of the several figures of the drawing.

BRIEF DESCRIPTION OF THE DRAWINGS

FIG. 5 is a perspective detailed view of a capstan drive mechanism used for two degrees of motion in the present invention;

FIG. 5a is a side elevational view of the capstan drive mechanism shown in FIG. 5;

FIG. 5b is a detailed side view of a pulley and cable of the capstan drive mechanism of FIG. 5;

FIG. 6 is a perspective view of a center capstan drive mechanism for a linear axis member of the mechanical apparatus shown in FIG. 3;

FIG. 6a is a cross sectional top view of a pulley and linear axis member used in the capstan drive mechanism of FIG. 6;

FIG. 6b is a cross sectional side view of the linear axis member and transducer shown in FIG. 6;

FIG. 12b is a schematic diagram of an alternate embodiment of the transducer system of FIG. 12a;

FIG. 13 is a schematic diagram of the transducer system of FIG. 12a which provides backlash between an actuator and an object;

FIG. 14a is a sectional side view of the actuator shaft and coupling of the transducer system of FIG. 13;

FIG. 14b is a sectional side view of the actuator shaft and coupling of FIG. 14a;

FIG. 15 is a detailed view of the keyed portions, of the actuator shaft and coupling of FIG. 14a;

DETAILED DESCRIPTION OF PREFERRED EMBODIMENTS

Figure 1:
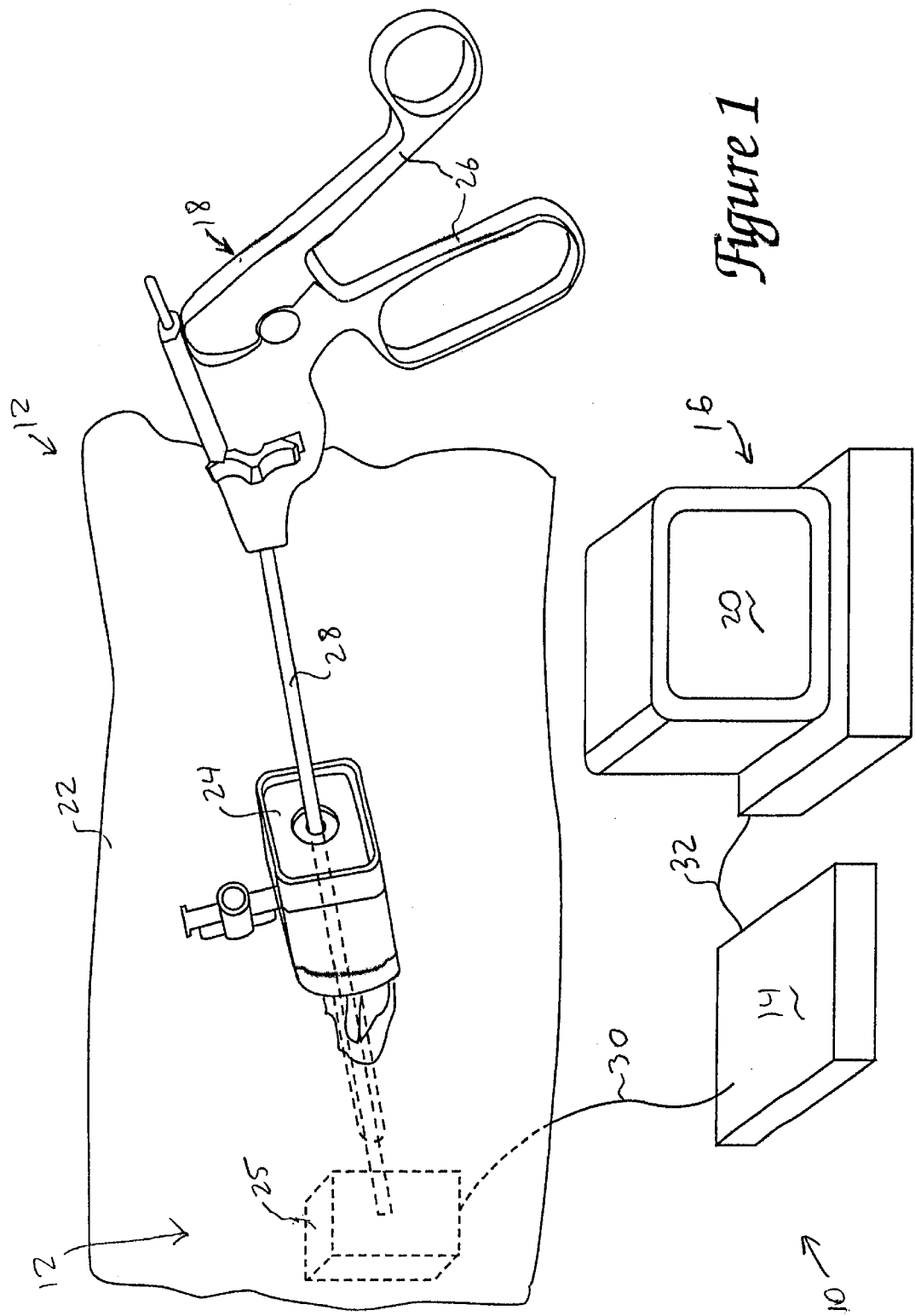
FIG. 1 is a perspective view of a virtual reality system which employs an apparatus of the present invention to interface a laparscope tool handle with a computer system.

In FIG. 1, a virtual reality system 10 used to simulate a medical procedure includes a human/computer interface apparatus 12, an electronic interface 14, and a computer 16. The illustrated virtual reality system 10 is directed to a virtual reality simulation of a laparoscopic surgery procedure. The software of the simulation is not a part of this invention and thus will not be discussed in any detail. However, such software is commercially available as, for example, Teleos™ from High Techsplanations of Rockville, Md. Suitable software drivers which interface such simulation software with computer input/output (I/O) devices are available from Immersion Human Interface Corporation of Santa Clara, Calif.

The handle 26 of a laparoscopic tool 18 used in conjunction with the present invention is manipulated by an operator and virtual reality images are displayed on a screen 20 of the digital processing system in response to such manipulations. Preferably, the digital processing system is a personal computer or workstation, such as an IBM-PC AT or Macintosh personal computer, or a SUN or Silicon Graphics workstation. Most commonly, the digital processing system is a personal computer which operates under the MS-DOS operating system in conformance with an IBM PC AT standard.

The human/interface apparatus 12 as illustrated herein is used to simulate a laparoscopic medical procedure. In addition to the handle of a standard laparoscopic tool 18, the human/interface apparatus 12 may include a barrier 22 and a standard laparoscopic trocar 24 (or a facsimile of a trocar). The barrier 22 is used to represent portion of the skin covering the body of a patient. Trocar 24 is inserted into the body of the virtual patient to provide an entry and removal point from the body of the patient for the laparoscopic tool 18, and to allow the manipulation of the laparoscopic tool. Laparoscopic tools and trocars 24 are commercially available from sources such as U.S. Surgical of Connecticut. Barrier 22 and trocar 24 can be omitted from apparatus 12 in other embodiments. Preferably, the laparoscopic tool 18 is modified; in the preferred embodiment, the shaft is replaced by a linear axis member of the present invention, as described below. In other embodiments, the end of the shaft of the tool (such as any cutting edges) can be removed. The end of the laparoscopic tool 18 is not required for the virtual reality simulation, and is removed to prevent any potential damage to persons or property. An apparatus 25 for interfacing mechanical input and output is shown within the "body" of the patient in phantom lines.

The laparoscopic tool 18 includes a handle or "grip" portion 26 and a shaft portion 28. The shaft portion is an elongated mechanical object and, in particular, is an elongated cylindrical object, described in greater detail below. In one embodiment, the present invention is concerned with tracking the movement of the shaft portion 28 in three-dimensional space, where the movement has been constrained such that the shaft portion 28 has only three or four free degrees of motion. This is a good simulation of the real use of a laparoscopic tool 18 in that once it is inserted into a trocar 24 and through the gimbal apparatus 25, it is limited to about four degrees of freedom. More particularly, the shaft 28 is constrained at some point along its length such that it can move with four degrees of freedom within the patient's body.

While one embodiment of the present invention will be discussed with reference to the laparoscopic tool 18, it will be appreciated that a great number of other types of objects can be used with the method and apparatus of the present invention. In fact, the present invention can be used with any mechanical object where it is desirable to provide a human/computer interface with three to six degrees of freedom. Such objects may include endoscopic or other similar surgical tools used in medical procedures, catheters, hypodermic needles, wires, fiber optic bundles, styluses, joysticks, screw drivers, pool cues, etc. Some of these other objects are described in detail subsequently.

The electronic interface 14 is a component of the human/computer interface apparatus 12 and couples the apparatus 12 to the computer 16. More particularly, interface 14 is used in preferred embodiments to couple the various actuators and sensors contained in apparatus 12 (which actuators and sensors are described in detail below) to computer 16. A suitable interface 14 is described in detail with reference to FIG. 9.

The electronic interface 14 is coupled to mechanical apparatus 25 of the apparatus 12 by a cable 30 and is coupled to the computer 16 by a cable 32. In other embodiments, signal can be sent to and from interface 14 and computer 16 by wireless transmission and reception. In some embodiments of the present invention, interface 14 serves solely as an input device for the computer 16. In other embodiments of the present invention, interface 14 serves solely as an output device for the computer 16. In preferred embodiments of the present invention, the interface 14 serves as an input/output (I/O) device for the computer 16.

Figure 2:
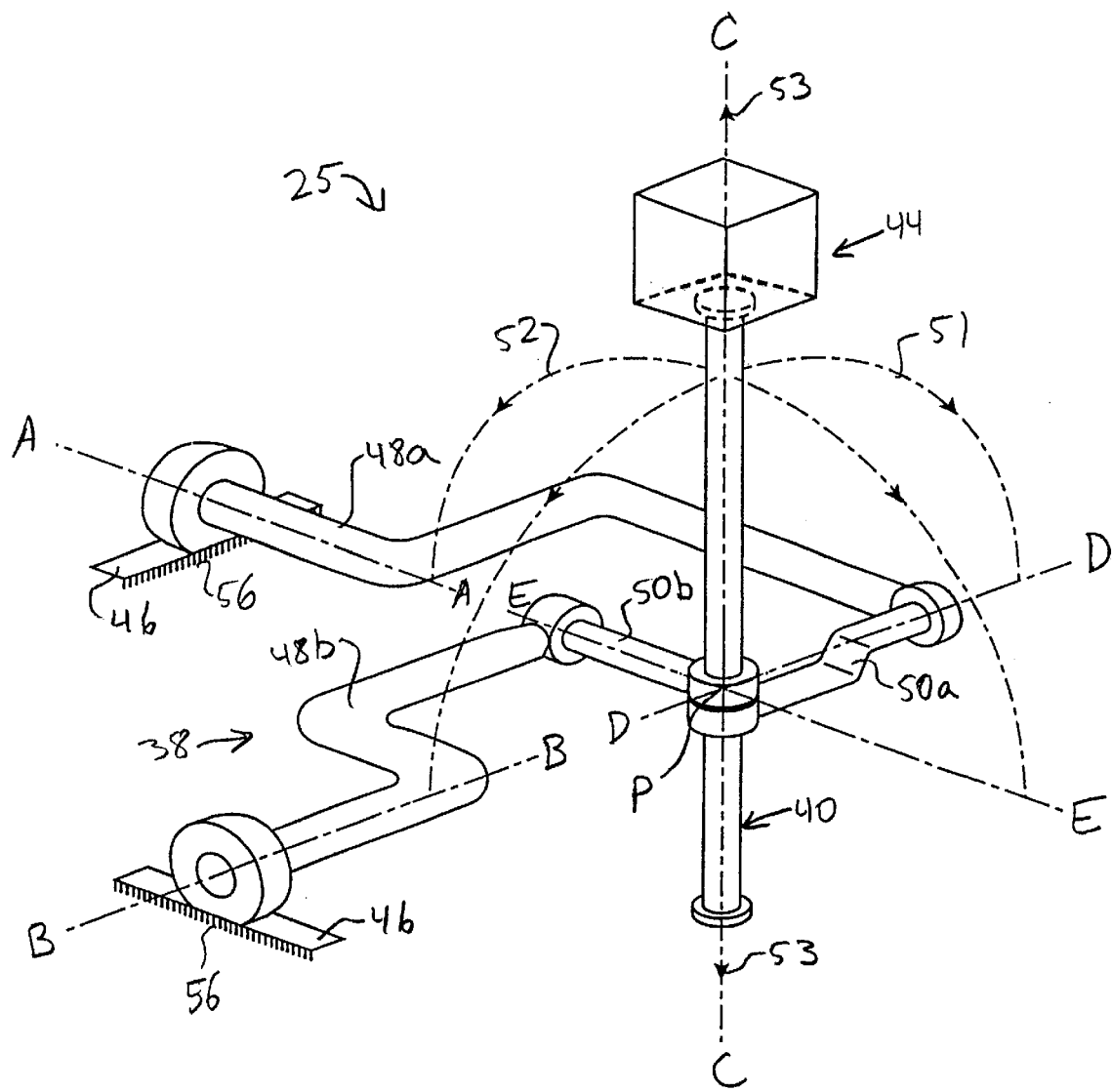
FIG. 2 is a schematic diagram of a mechanical apparatus of the present invention for providing mechanical input and output to a computer system.

In FIG. 2, a schematic diagram of mechanical apparatus 25 for providing mechanical input and output in accordance with the present invention is shown. Apparatus 25 includes a gimbal mechanism 38 and a linear axis member 40. A user object 44 is preferably coupled to linear axis member 40.

Gimbal mechanism 38, in the described embodiment, provides support for apparatus 25 on a grounded surface 56 (schematically shown as part of member 46). Gimbal mechanism 38 is preferably a five-member linkage that includes a ground member 46, extension members 48a and 48b, and central members 50a and 50b. Ground member 46 is coupled to a base or surface which provides stability for apparatus 25. Ground member 46 is shown in FIG. 2 as two separate members coupled together through grounded surface 56. The members of gimbal mechanism 38 are rotatably coupled to one another through the use of bearings or pivots, wherein extension member 48a is rotatably coupled to ground member 46 and can rotate about an axis A, central member 50a is rotatably coupled to extension member 48a and can rotate about a floating axis D, extension member 48b is rotatably coupled to ground member 46 and can rotate about axis B, central member 50b is rotatably coupled to extension member 48b and can rotate about floating axis E, and central member 50a is rotatably coupled to central member 50b at a center point P at the intersection of axes D and E. The axes D and E are "floating" in the sense that they are not fixed in one position as are axes A and B. Axes A and B are substantially mutually perpendicular. As used herein, "substantially perpendicular" will mean that two objects or axis are exactly or almost perpendicular, i.e. at least within five degrees or teen degrees of perpendicular, or more preferably within less than one degree of perpendicular. Similarly, the term "substantially parallel" will mean that two objects or axis are exactly or almost parallel, i.e., are at least within five or ten degrees of parallel, and are preferably within less than one degree of parallel.

Gimbal mechanism 38 is formed as a five member closed chain. Each end of one member is coupled to the end of an another member. The five-member linkage is arranged such that extension member 48a, central member 50a, and central member 50b can be rotated about axis A in a first degree of freedom. The linkage is also arranged such that extension member 48b, central member 50b, and central member 50a can be rotated about axis B in a second degree of freedom.

Linear axis member 40 is preferably an elongated rod-like member which is coupled to central member 50a and central member 50b at the point intersection P of axes A and B. As shown in FIG. 1, linear axis member 40 can be used as shaft 28 of user object 44. In other embodiments, linear axis member 40 is coupled to a different object. Linear axis member 40 is coupled to gimbal mechanism 38 such that it extends out of the plane defined by axis A and axis B. Linear axis member 40 can be rotated about axis A by rotating extension member 48a, central member 50a, and central member 50b in a first revolute degree of freedom, shown as arrow line 51. Member 40 can be rotated about axis B by rotating extension member 50b and the two central members about axis B in a second revolute degree of freedom, shown by arrow line 52. Being also translatably coupled to the ends of central members 50a and 50b, linear axis member 40 can be linearly moved along floating axis C, providing a third degree of freedom as shown by arrows 53. Axis C can, of course, be rotated about one or both axes A and B as member 40 is rotated about these axes.

Also preferably coupled to gimbal mechanism 38 and linear axis member 40 are transducers, such as sensors and actuators. Such transducers are preferably coupled at the link points between members of the apparatus and provide input to and output from an electrical system, such as computer 16. Transducers that can be used with the present invention are described in greater detail with respect to FIG. 2.

User object 44 is coupled to apparatus 25 and is preferably an interface object for a user to grasp or otherwise manipulate in three dimensional (3D) space. One preferred user object 44 is the grip 26 of a laparoscopic tool 18, as shown in FIG. 1. Shaft 28 of tool 18 can be implemented as part of linear axis member 40. Other examples of user objects are described in subsequent embodiments. User object 44 may be moved in all three degrees of freedom provided by gimbal mechanism 38 and linear axis member 40 and additional degree of freedom as described below. As user object 44 is moved about axis A, floating axis D varies its position, and as user object 44 is moved about axis B, floating axis E varies its position.

Figure 3:
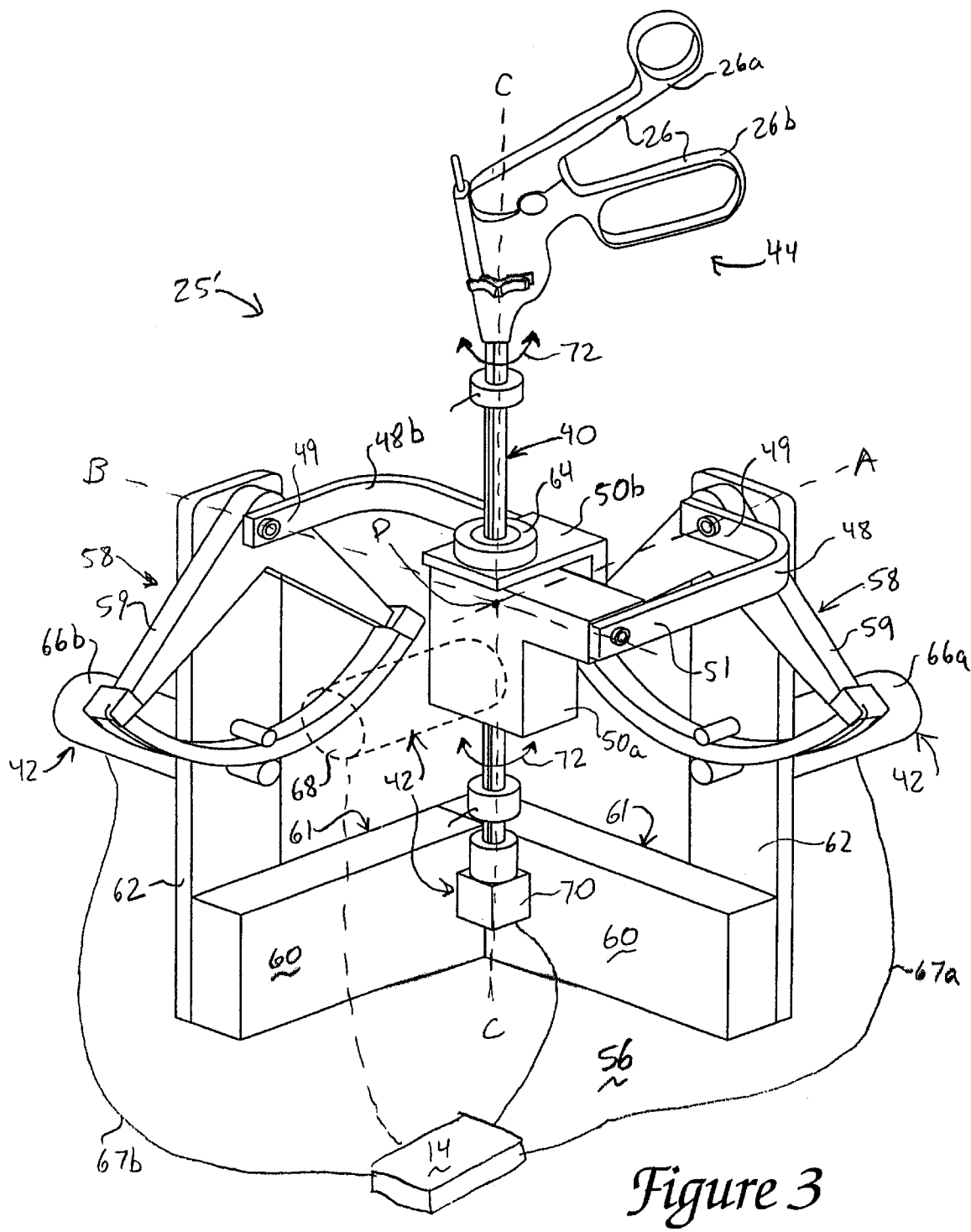
FIG. 3 is a perspective front view of a preferred embodiment of the mechanical apparatus of FIG. 2.
Figure 4:
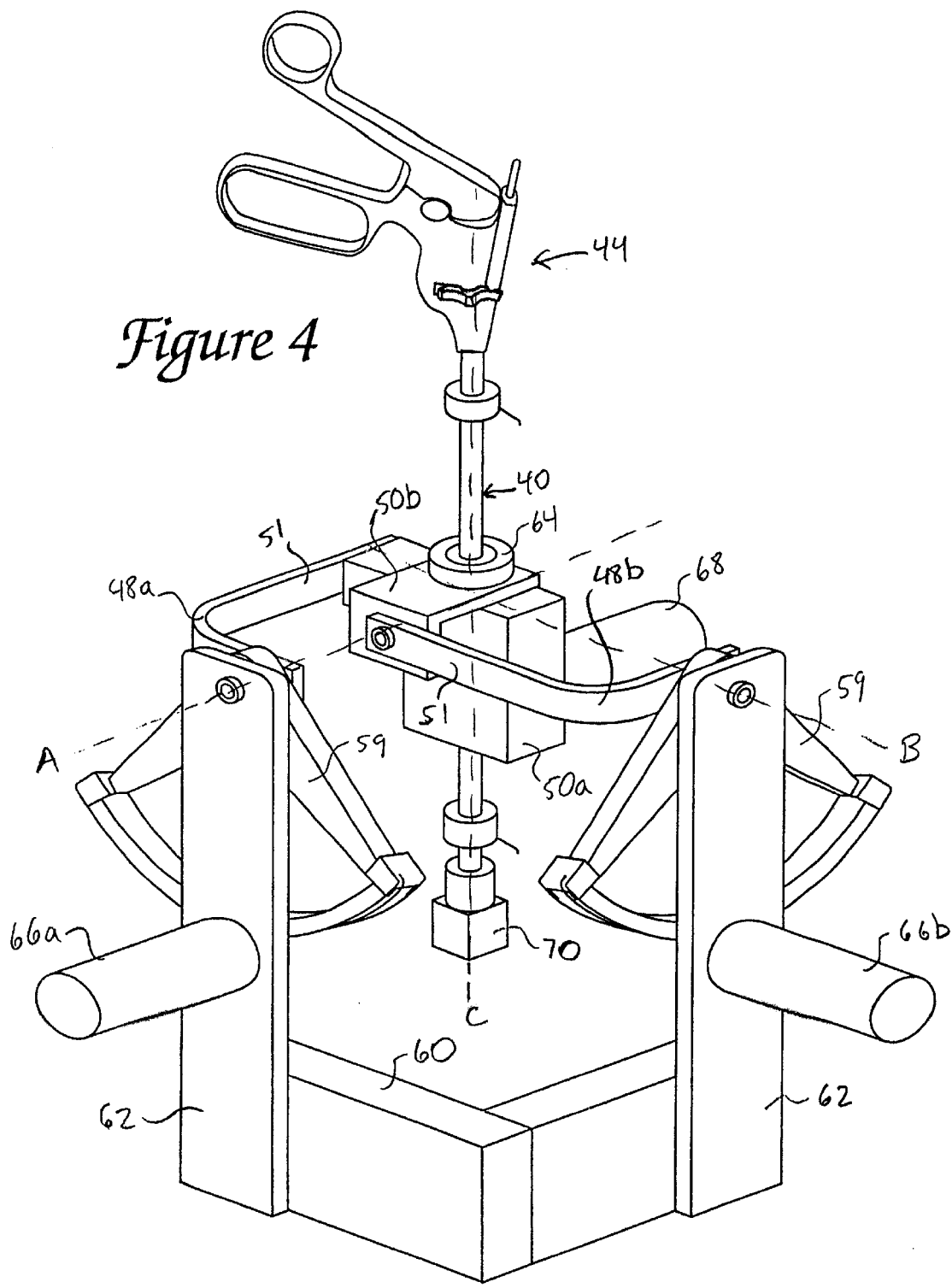
FIG. 4 is a perspective rear view of the embodiment of the mechanical apparatus of FIG. 3.

FIGS. 3 and 4 are perspective views of a specific embodiment of a mechanical apparatus 25' for providing mechanical input and output to a computer system in accordance with the present invention. FIG. 3 shows a front view of apparatus 25', and FIG. 4 shows a rear view of the apparatus. Apparatus 25' includes a gimbal mechanism 38, a linear axis member 40, and transducers 42. A user object 44, shown in this embodiment as a laparoscopic instrument having a grip portion 26, is coupled to apparatus 25'. Apparatus 25' operates in substantially the same fashion as apparatus 25 described with reference to FIG. 2.

Gimbal mechanism 38 provides support for apparatus 25' on a grounded surface 56, such as a table top or similar surface. The members and joints ("bearings") of gimbal mechanism 38 are preferably made of a lightweight, rigid, stiff metal, such as aluminum, but can also be made of other rigid materials such as other metals, plastic, etc. Gimbal mechanism 38 includes a ground member 46, capstan drive mechanisms 58 extension members 48a and 48b, central drive member 50a, and central link member 50b. Ground member 46 includes a base member 60 and vertical support members 62. Base member 60 is coupled to grounded surface 56 and provides two outer vertical surfaces 61 which are in a substantially perpendicular relation which each other. A vertical support member 62 is coupled to each of these outer surfaces of base member 60 such that vertical members 62 are in a similar substantially 90-degree relation with each other.

A capstan drive mechanism 58 is preferably coupled to each vertical member 62. Capstan drive mechanisms 58 are included in gimbal mechanism 38 to provide mechanical advantage without introducing friction and backlash to the system. A capstan drum 59 of each capstan drive mechanism is rotatably coupled to a corresponding vertical support member 62 to form axes of rotation A and B, which correspond to axes A and B as shown in FIG. 2. The capstan drive mechanisms 58 are described in greater detail with respect to FIG. 5.

Extension member 48a is rigidly coupled to capstan drum 59 and is rotated about axis A as capstan drum 59 is rotated. Likewise, extension member 48b is rigidly coupled to the other capstan drum 59 and can be rotated about axis B. Both extension members 48a and 48b are formed into a substantially 90-degree angle with a short end 49 coupled to capstan drum 59. Central drive member 50a is rotatably coupled to a long end 55 of extension member 48a and extends at a substantially parallel relation with axis B. Similarly, central link member 50b is rotatably coupled to the long end of extension member 48b and extends at a substantially parallel relation to axis A (as better viewed in FIG. 4). Central drive member 50a and central link member 50b are rotatably coupled to each other at the center of rotation of the gimbal mechanism, which is the point of intersection P of axes A and B. Bearing 64 connects the two central members 50a and 50b together at the intersection point P.

Gimbal mechanism 38 provides two degrees of freedom to an object positioned at or coupled to the center point P of rotation. An object at or coupled to point P can be rotated about axis A and B or have a combination of rotational movement about these axes.

Linear axis member 40 is a cylindrical member that is preferably coupled to central members 50a and 50b at intersection point P. In alternate embodiments, linear axis member 40 can be a non-cylindrical member having a cross-section of, for example, a square or other polygon. Member 40 is positioned through the center of bearing 64 and through holes in the central members 50a and 50b. The linear axis member can be linearly translated along axis C, providing a third degree of freedom to user object 44 coupled to the linear axis member. Linear axis member 40 can preferably be translated by a transducer 42 using a capstan drive mechanism similar to capstan drive mechanism 58. The translation of linear axis member 40 is described in greater detail with respect to FIG. 6.

Transducers 42 are preferably coupled to gimbal mechanism 38 to provide input and output signals between mechanical apparatus 25' and computer 16. In the described embodiment, transducer 42 include two grounded transducers 66a and 66b, central transducer 68, and shaft transducer 70. The housing of grounded transducer 66a is preferably coupled to vertical support member 62 and preferably includes both an actuator for providing force in or otherwise influencing the first revolute degree of freedom about axis A and a sensor for measuring the position of object 44 in or otherwise influenced by the first degree of freedom about axis A, i.e., the transducer 66a is "associated with" or "related to" the first degree of freedom. A rotational shaft of actuator 66a is coupled to a pulley of capstan drive mechanism 58 to transmit input and output along the first degree of freedom. The capstan drive mechanism 58 is described in greater detail with respect to FIG. 5. Grounded transducer 66b preferably corresponds to grounded transducer 66a in function and operation. Transducer 66b is coupled to the other vertical support member 62 and is an actuator/sensor which influences or is influenced by the second revolute degree of freedom about axis B.

Grounded transducers 66a and 66b are preferably bi-directional transducers which include sensors and actuators. The sensors are preferably relative optical encoders which provide signals to measure the angular rotation of a shaft of the transducer. The electrical outputs of the encoders are routed to computer interface 14 via buses 67a and 67b and are detailed with reference to FIG. 9. Other types of sensors can also be used, such as potentiometers, etc.

It should be noted that the present invention can utilize both absolute and relative sensors. An absolute sensor is one which the angle of the sensor is known in absolute terms, such as with an analog potentiometer. Relative sensors only provide relative angle information, and thus require some form of calibration step which provide a reference position for the relative angle information. The sensors described herein are primarily relative sensors. In consequence, there is an implied calibration step after system power-up wherein the sensor's shaft is placed in a known position within the apparatus 25' and a calibration signal is provided to the system to provide the reference position mentioned above. All angles provided by the sensors are thereafter relative to that reference position. Such calibration methods are well known to those skilled in the art and, therefore, will not be discussed in any great detail herein.

Transducers 66a and 66b also preferably include actuators which, in the described embodiment, are linear current control motors, such as DC serve motors. These motors preferably receive current signals to control the direction and torque (force output) that is produced on a shaft; the control signals for the motor are produced by computer interface 14 on control buses 67a and 67b and are detailed with respect to FIG. 9. The motors may include brakes which allow the rotation of the shaft to be halted in a short span of time. A suitable transducer for the present invention including both an optical encoder and current controlled motor is a 20 W basket wound servo motor manufactured by Maxon of Burlingame, Calif.

In alternate embodiments, other types of motors can be used, such as a stepper motor controlled with pulse width modulation of an applied voltage, or pneumatic motors. However, the present invention is much more suited to the user of linear current controlled motors. This is because voltage pulse width modulation or stepper motor control involves the use of steps or pulses which can be felt as "noise" by the user. Such noise currupts the virtual simulation. Linear current control is smoother and thus more appropriate for the present invention.

Passive actuators can also be used in transducer 66a, 66b and 68. Magnetic particle brakes or friction brakes can be used in addition to or instead of a motor to generate a passive resistance or friction in a degree of motion. An alternate preferred embodiment only including passive actuators may not be as realistic as an embodiment including motors; however, the passive actuators are typically safer for a user since the user does not have to fight generated forces.

In other embodiments, all or some of transducers 42 can include only sensors to provide an apparatus without force feedback along designated degrees of freedom. Similarly, all or some of transducers 42 can be implemented as actuators without sensors to provide only force feedback.

Central transducer 68 is coupled to central drive member 50a and preferably includes an actuator for providing force in the linear third degree of freedom along axis C and a sensor for measuring the position of object 44 along the third degree of freedom. The rotational shaft of central transducer 68 is coupled to a translation interface coupled to central drive member 50a which is described in greater detail with respect to FIG. 6. In the described embodiment, central transducer 68 is an optical encoder and DC servo motor combination similar to the actuators 66a and 66b described above.

The transducers 66a, 66b and 68 of the described embodiment are advantageously positioned to provide a very low amount of inertia to the user handling object 44. Transducer 66a and transducer 66b are decoupled, meaning that the transducers are both directly coupled to ground member 46 which is coupled to ground surface 56, i.e. the ground surface carriers the weight of the transducers, not the user handling object 44. The weights and inertia of the transducers 66a and 66b are thus substantially negligible to a user handling and moving object 44. This provides a more realistic interface to a virtual reality system, since the computer can control the transducers to provide substantially all of the forces felt by the user in these degrees of motion. Apparatus 25' is a high bandwidth force feedback system, meaning that high frequency signals can be used to control transducers 42 and these high frequency signals will be applied to the user object with high precision, accuracy, and dependability. The user feels very little compliance or "mushiness" when handling object 44 due to the high bandwidth. In contrast, in typical prior art arrangements of multi-degree of freedom interfaces, one actuator "rides" upon another actuator in a serial chain of links and actuators. This low bandwidth arrangement causes the user to feel the inertia of coupled actuators when manipulating an object.

Central transducer 68 is positioned near the center of rotation of two revolute degrees of freedom. Though the transducer 68 is not grounded, its central position permits a minimal inertial contribution to the mechanical apparatus 25' along the provided degrees of freedom. A user manipulating object 44 thus will feel minimal internal effects from the weight of transducers 66a 66b and 68.

Shaft transducer 70 preferably includes a sensor and is provided in the described embodiment to measure a fourth degree of freedom for object 44. Shaft transducer 70 is preferably positioned at the end of linear axis member 40 that is opposite to the object 44 and measures the rotational position of object 44 about axis C in the fourth degree of freedom, an indicated by arrow 72. Shaft transducer 70 is described in greater detail withrespect to FIGS. 6 and 6b. Preferably, shaft transducer 72 is implemented using an optical encoder similar to the encoders described above. A suitable input transducer for use in the present invention is an optical encoder model SI marketed by U.S. Digital of Vancouver, Wash. In the described embodiment, shaft transducer 70 only includes a sensor and not an actuator. This is because for typical medical procedures, which is one intended application for the embodiment shown in FIGS. 3 and 4, rotational force feedback to a user about axis C is typically not required to simulate actual operating conditions. However, in alternate embodiments, an actuator such as a motor can be included in shaft transducer 70 similar to transducers 66a, 66b, and 68.

Object 44 is shown in FIGS. 3 and 4 as a grip portion 26 of a laparoscopic tool similar to the tool shown in FIG. 1. Shaft portion 28 is implemented as linear axis member 40. A user can move the laparoscopic tool above axes A and B, and can translate the tool along axis C and rotate the tool about axis C. The movements in these four degrees of freedom will be sensed and tracked by computer system 16. Forces can be applied preferably in the first three degrees of freedom by the computer system to simulate the tool impacting a portion of subject body, experiencing resistance moving through tissues, etc.

Optionally, additional transducers can be added to apparatus 25' to provide additional degrees of freedom for object 44. For example, a transducer can be added to grip 26 of laparoscopic tool 18 to sense when the user moves the two portions 26a and 26b relative to each other to simulate extending the cutting blade of the tool. Such a laparoscopic tool sensor is described in U.S. patent application Ser. No. 08/275,120, now U.S. Pat. No. 5,623,582 filed Jul. 14, 1994 and entitled "Method and Apparatus for Providing Mechanical I/O for Computer Systems" assigned to the assignee of the present invention and incorporated herein by reference in its entirety.

FIG. 5 is a perspective view of a capstan drive mechanism 58 shown in some detail. As an example, the drive mechanism 58 coupled to extension arm 48b is shown; the other capstan drive 58 coupled to extension arm 48a is substantially similar to the mechanism presented here. Capstan drive mechanism 58 includes capstan drum 59, capstan pulley 76, and stop 78. Capstan drum 59 is preferably a wedge-shaped member having leg portion 82 and a curved portion 84. Other shapes of member 59 can also be used. Leg portion 82 is pivotally coupled to vertical support member 62 at axis B (or axis A for the opposing capstan drive mechanism). Extension member 48b is rigidly coupled to leg portion 82 such that when capstan drum 59 is rotated about axis B, extension member 48b is also rotated and maintains the position relative to leg portion 82 as shown in FIG. 5. Curved portion 84 couples the two ends of leg portion 82 together and is preferably formed in an arc centered about axis B. Curved portion 84 is preferably positioned such that its bottom edge 86 is about 0.030 inches above pulley 76.

Cable 80 is preferably a thin metal cable connected to curved portion 84 of the capstan drum. Other types of durable cables, cords, wire, etc. can be used as well. Cable 80 is attached at a first end to curved portion 84 near an end of leg portion 82 and is drawn tautly against the outer surface 86 of curved portion 84. Cable 80 is wrapped around pulley 76 a number of times and is then again drawn tautly against outer surface 86. The second end of cable 80 is firmly attached to the other end of curved portion 84 near the opposite leg of leg portion 82. The cable transmits rotational force from pulley 76 to the capstan drum 59, causing capstan drum 59 to rotate about axis B as explained below. The cable also transmits rotational force from drum 59 to the pulley and transducer 66b. The tension in cable 80 should be at a level so that negligible backlash or play occurs between capstan drum 59 and pulley 76. Preferably, the tension of cable 80 can be adjusted by pulling more (or less) cable length through an end of curved portion 84. Caps 81 on the ends of curved portion 84 can be used to easily tighten cable 80. Each cap 81 is preferably tightly coupled to cable 80 and includes a pivot and tightening screw which allow the cap to move in a direction indicated by arrow 83 to tighten cable 80.

Capstan pulley 76 is a threaded metal cylinder which transfers rotational force from transducer 66b to capstan drum 59 and from capstan drum 59 to transducer 66b. Pulley 76 is rotationally coupled to vertical support member 62 by a shaft 88 (shown in FIG. 5a) positioned through a bore of vertical member 62 and rigidly attached to pulley 76. Transducer 66b is coupled to pulley 76 by shaft 88 through vertical support member 62. Rotational force is applied from transducer 66b to pulley 76 when the actuator of transducer 66b rotates the shaft. The pulley, in turn, transmits the rotational force to cable 80 and thus forces capstan drum 59 to rotate in a direction about axis B. Extension member 48b rotates with capstan drum 59, thus causing force along the second degree of freedom for object 44. Note that pulley 76, capstan drum 59 and extension member 48b will only actually rotate if the user is not applying the same amount or a greater amount of rotational force to object 44 in the opposite direction to cancel the rotational movement. In any event, the user will feel the rotational force along the second degree of freedom in object 44 as force feedback.

The capstan mechanism 58 provides a mechanical advantage to apparatus 25' so that the force output of the actuators can be increased. The ratio of the diameter of pulley 76 to the diameter of capstan drum 59 (i.e. double the distance from axis B to the bottom edge 86 of capstan drum 59) dictates the amount of mechanical advantage, similar to a gear system. In the preferred embodiment, the ratio of drum to pulley is equal to 15:1, although other ratios can be used in other embodiments.

Similarly, when the user moves object 44 in the second degree of freedom, extension member 48b rotates about axis B and rotates capstan drum 59 about axis B as well. This movement causes cable 80 to move, which transmits the rotational force to pulley 76. Pulley 76 rotates and causes shaft 88 to rotate, and the direction and magnitude of the movement is detected by the sensor of transducer 66b. A similar process occurs along the first degree of freedom for the other capstan drive mechanism 58. As described above with respect to the actuators, the capstan drive mechanism provides a mechanical advantage to amplify the sensor resolution by a ratio of drum 59 to pulley 76 (15:1 in the preferred embodiment).

Stop 78 is rigidly coupled to vertical support member 62 a few millimeters above curved portion 84 of capstan drum 59. Stop 78 is used to prevent capstan drum 59 from moving beyond a designated angular limit. Thus, drum 59 is constrained to movement within a range defined by the arc length between the ends of leg portion 82. This constrained movement, in turn, constrains the movement of object 44 in the first two degrees of freedom. In the described embodiment, stop 78 is a cylindrical member inserted into a threaded bore in vertical support member 62.

FIG. 5a is a side elevational view of capstan mechanism 58 as shown in FIG. 5. Cable 80 is shown routed along the bottom side 86 of curved portion 84 of capstan drum 59. Cable 80 is preferably wrapped around pulley 76 so that the cable is positioned between threads 90, i.e., the cable is guided by the threads as shown in greater detail in FIG. 5b. As pulley 76 is rotated by transducer 66b or by the manipulations of the user, the portion of cable 80 is wrapped around the pulley travels closer to or further from vertical support member 62, depending on the direction that pulley 76 rotates. For example, if pulley 76 is rotated counterclockwise (when viewing the pulley as in FIG. 5), the cable 80 moves toward vertical support member 62 as shown by arrow 92. Capstan drum 59 also rotates clockwise as shown by arrow 94. The threads of pulley 76 are used mainly to provide cable 80 with a better grip on pulley 76. In alternate embodiments, pulley 76 includes no threads, and the high tension in cable 80 allows cable 80 to grip pulley 76.

Capstan drive mechanism 58 is advantageously used in the present invention to provide transmission of forces and mechanical advantage between transducers 66a and 66b and object 44 without introducing substantial compliance, friction, or backlash to the system. A capstan drive provides increased stiffness, so that forces are transmitted with negligible stretch and compression of the components. The amount of friction is also reduced with a capstan drive mechanism so that substantially "noiseless" tactile signals can be provided to the user. In addition, the amount of backlash contributed by a capstan drive is also negligible. "Backlash" is the amount of play that occurs between two coupled rotating objects in a gear or pulley system. Two gears, belts, or other types of drive mechanisms could also be used in place of capstan drive mechanism 58 in alternate embodiments to transmit forces between transducer 66a and extension member 48b. However, gears and the like typically introduce some backlash in the system. In addition, a user might be able to feel the interlocking and grinding of gear teeth during rotation of gears when manipulating object 44; the rotation in a capstan drive mechanism is much less noticeable.

FIG. 6 is a perspective view of central drive member 50a and linear axis member 40 shown in some detail. Central drive member 50a is shown in a partial cutaway view to expose the interior of member 50a. Central transducer 68 is coupled to one side of central drive member 50a. In the described embodiment, a capstan drive mechanism is used to transmit forces between transducer 68 and linear axis member 40 along the third degree of freedom. A rotatable shaft 98 of transducer 68 extends through a bore in the side wall of central drive member 50a and is coupled to a capstan pulley 100. Pulley 100 is described in greater detail below with respect to FIG. 6a.

Linear axis member 40 preferably includes an exterior sleeve 91 and an interior shaft 93 (described with reference to FIG. 6b, below). Exterior sleeve 91 is preferably a partially cylindrical member having a flat 41 provided along its length. Flat 41 prevents sleeve 91 from rotating about axis C in the fourth degree of freedom described above. Linear axis member 40 is provided with a cable 99 which is secured on each end of member 40 by tension caps 101. Cable 99 preferably runs down a majority of the length of exterior sleeve 91 on the surface of flat 41 and can be tightened, for example, by releasing a screw 97, pulling an end of cable 99 until the desired tension is achieved, and tightening screw 97. Similarly to the cable of the capstan mechanism described with reference to FIG. 5, cable 99 should have a relatively high tension.

As shown in FIG. 6a, cable 99 is wrapped a number of times around pulley 100 so that forces can be transmitted between pulley 100 and linear axis member 40. Pulley 100 preferably includes a central axle portion 103 and end lip portions 105. Exterior sleeve 91 is preferably positioned such that flat 41 of the sleeve is touching or is very close to lip portions 105 on both sides of axle portion 103. The cable 99 portion around pulley 100 is wrapped around central axle portion 103 and moves along portion 103 towards and away from shaft 98 as the pulley is rotated clockwise and counterclockwise, respectively. The diameter of axle portion 103 is smaller than lip portion 105, providing space between the pulley 100 and flat 41 where cable 99 is attached and allowing free movement of the cable. Pulley 100 preferably does not include threads, unlike pulley 76, since the tension in cable 99 allows the cable to grip pulley 100 tightly. In other embodiments, pulley 100 can be a threaded or unthreaded cylinder similar to capstan pulley 76 described with reference to FIG. 5.

Using the capstan drive mechanism, transducer 68 can translate linear axis member 40 along axis C when the pulley is rotated by the actuator of transducer 68. Likewise, when linear axis member 40 is translated along axis C by the user manipulating object 44, pulley 100 and shaft 98 are rotated; this rotation is detected by the sensor of transducer 68. The capstan drive mechanism provides low friction and smooth, rigid operation for precise movement of linear axis member 40 and accurate position measurement of the member 40.

Other drive mechanisms can also be used to transmit forces to linear axis member and receive positional information from member 40 along axis C. For example, a drive wheel made of a rubber-like material or other frictional material can be positioned on shaft 98 to contact linear axis member 40 along the edge of the wheel. The wheel can cause forces along member 40 from the friction between wheel and linear axis member. Such a drive wheel mechanism is disclosed in the abovementioned application Ser. No. 08/275,120 now U.S. Pat. No. 5,623,582 as well as in U.S. patent application Ser. No. 08/344,148, filed Nov. 23, 1994 and entitled "Method and Apparatus for Providing Mechanical I/O for Computer Systems Interfaced with Elongated Flexible Objects" assigned to the assignee of the present invention and incorporated herein by reference in its entirety. Linear axis member 40 can also be a single shaft in alternate embodiments instead of a dual part sleeve and shaft.

Referring to the cross sectional side view of member 40 and transducer 70 shown in FIG. 6b, interior shaft 93 is positioned inside hollow exterior sleeve 91 and is rotatably coupled to sleeve 91. A first end 107 of shaft 93 preferably extends beyond sleeve 91 and is coupled to object 44. When object 44 is rotated about axis C, shaft 93 is also rotated about axis C in the fourth degree of freedom within sleeve 91. Shaft 93 is translated along axis C in the third degree of freedom when sleeve 91 is translated. Alternatively, interior shaft 93 can be coupled to a shaft of object 44 within exterior sleeve 91. For example, a short portion of shaft 28 of laparoscopic tool 18, as shown in FIG. 1, can extend into sleeve 91 and be coupled to shaft 93 within the sleeve, or shaft 28 can extend all the way to transducer 70 and functionally be used as shaft 93.

Shaft 93 is coupled at its second end 109 to transducer 70, which, in the preferred embodiment, is an optical encoder sensor. The housing 111 of transducer 70 is rigidly coupled to exterior sleeve 91 by a cap 115, and a shaft 113 of transducer 70 is coupled to interior shaft 93 so that transducer 70 can measure the rotational position of shaft 93 and object 44. In alternate embodiments, an actuator can also be included in transducer 70 to provide rotational forces about axis C to shaft 93.

Figure 7:
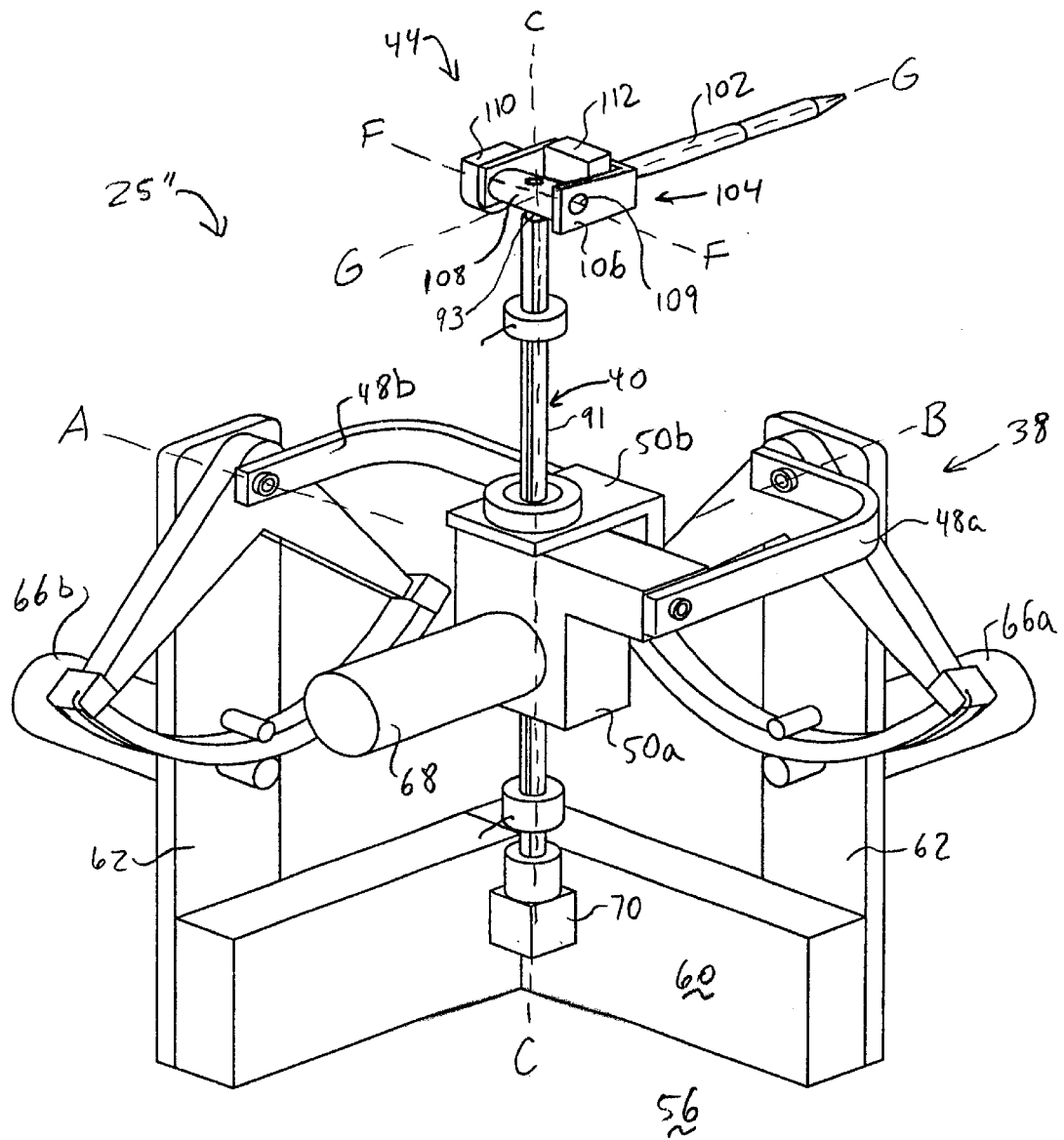
FIG. 7 is a perspective view of an embodiment of the apparatus of FIG. 2 having a stylus object for the user.

FIG. 7 is a perspective view of an alternate embodiment of the mechanical apparatus 25" and user object 44 of the present invention. Mechanical apparatus 25" shown in FIG. 7 operates substantially the same as apparatus 25' shown in FIGS. 3 and 4. User object 44, however, is a stylus 102 which the user can grasp and move in six degrees of freedom. By "grasp", it is meant that users may releasably engage a grip portion of the object in some fashion, such as by hand, with their fingertips, or even orally in the case of handicapped persons. Stylus 102 can be sensed and force can be applied in various degrees of freedom by a computer system and interface such as computer 16 and interface 14 of FIG. 1. Stylus 102 can be used in virtual reality simulations in which the user can move the stylus in 3D space to point to objects, write words, drawings, or other images, etc. For example, a user can view a virtual environment generated on a computer screen or in 3D goggles. A virtual stylus can be presented in a virtual hand of the user. The computer system tracks the position of the stylus with sensors as the user moves it. The computer system also provides force feedback to the stylus when the user moves the stylus against a virtual desk top, writes on a virtual pad of paper, etc. It thus appears and feels to the user that the stylus is contacting a real surface.

Stylus 102 preferably is coupled to a floating gimbal mechanism 104 which provides two degrees of freedom in addition to the four degrees of freedom provided by apparatus 25' described with reference to FIGS. 3 and 4. Floating gimbal mechanism 104 includes a U-shaped member 106 which is rotatably coupled to an axis member 108 by a shaft 109 so that U-shaped member 106 can rotate about axis F. Axis member 108 is rigidly coupled to linear axis member 40. In addition, the housing of a transducer 110 is coupled to U-shaped member 106 and a shaft of transducer 110 is coupled to shaft 109. Shaft 109 is preferably locked into position within axis member 108 so that as U-shaped member 106 is rotated, shaft 109 does not rotate. Transducer 110 is preferably a sensor, such as an optical encoder as described above with reference to transducer 70, which measures the rotation of U-shaped member 106 about axis F in a fifth degree of freedom and provides electrical signals indicating such movement to interface 14.

Stylus 102 is preferably rotatably coupled to U-shaped member 106 by a shaft (not shown) extending through the U-shaped member. This shaft is coupled to a shaft of transducer 112, the housing of which is coupled to U-shaped member 106 as shown. Transducer 112 is preferably a sensor, such as an optical encoder as described above, which measures the rotation of stylus 102 about the lengthwise axis G of the stylus in a sixth degree of freedom.

In the described embodiment of FIG. 7, six degrees of freedom of stylus 102 are sensed. Thus, both the position (x, y, z coordinates) and the orientation (roll, pitch, yaw) of the stylus can be detected by computer 16 to provide a highly realistic simulation. Other mechanisms besides the floating gimbal mechanism 104 can be used to provide the fifth and sixth degrees of freedom. In addition, forces can be applied in three degrees of freedom for stylus 102 to provide 3D force feedback. In alternate embodiments, actuators can also be included in transducers 70, 110, and 112. However, actuators are preferably not included for the fourth, fifth, and sixth degrees of freedom in the described embodiments, since actuators are typically heavier than sensors and, when positioned at the locations of transducers 70, 100, and 112, would create more inertia in the system. In addition, the force feedback for the designated three degrees of freedom allows impacts and resistance to be simulated, which is typically adequate in many virtual reality applications. Force feedback in the fourth, fifth, and sixth degrees of freedom would allow torques on stylus 102 to be simulated as well, which may or may not be useful in a simulation.

Figure 8:
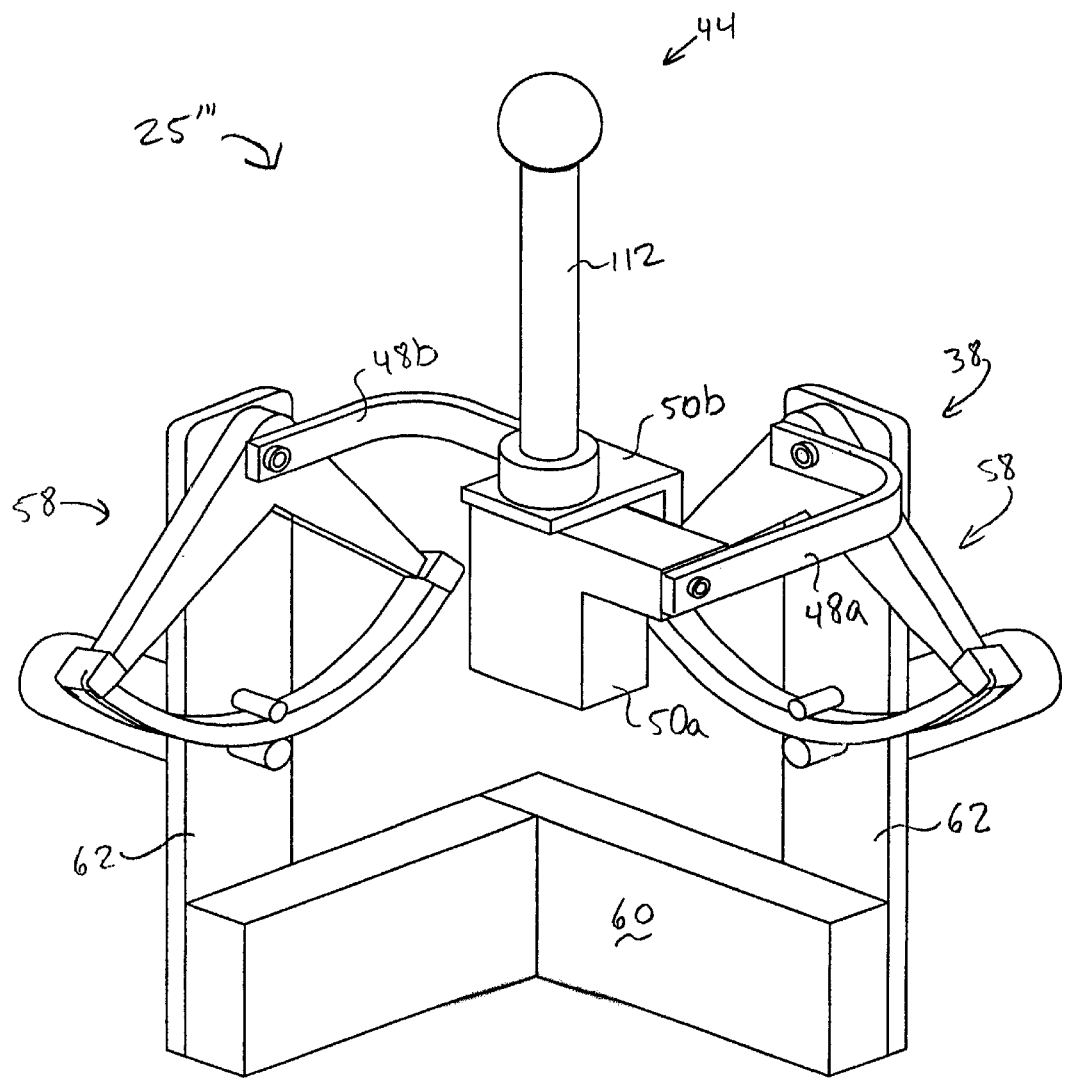
FIG. 8 is a perspective view of an embodiment of the apparatus of FIG. 2 having a joystick object for the user.

FIG. 8 is a perspective view of a second alternate embodiment of the mechanical apparatus 25''' and user object 44 of the present invention. Mechanical apparatus 25''' shown in FIG. 8 operates substantially the same as apparatus 25' shown in FIGS. 3 and 4. User object 44, however, is a joystick 112 which the user can preferably move in two degrees of freedom. Joystick 112 can be sensed and force can be applied in both degrees of freedom by a computer system and interface similar to computer system 16 and interface 14 of FIG. 1. In the described embodiment, joystick 112 is coupled to cylindrical fastener 64 so that the user can move the joystick in the two degrees of freedom provided by gimbal mechanism 38 as described above. Linear axis member 40 is not typically included in the embodiment of FIG. 8, since a joystick is not usually translated along an axis C. However, in alternate embodiments, joystick 112 can be coupled to linear axis member 40 similarly to stylus 102 as shown in FIG. 7 to provide a third degree of freedom. In yet other embodiments, linear axis member 40 can rotate about axis C and transducer 70 can be coupled to apparatus 25''' to provide a fourth degree of freedom. Finally, in other embodiments, a floating gimbal mechanism as shown in FIG. 7, or a different mechanism, can be added to the joystick to allow a full six degrees of freedom.

Joystick 112 can be used in virtual reality simulations in which the user can move the joystick to move a vehicle, point to objects, control a mechanism, etc. For example, a user can view a virtual environment generated on a computer screen or in 3D goggles in which joystick 112 controls an aircraft. The computer system tracks the position of the joystick as the user moves it around with sensors and updates the virtual reality display accordingly to make the aircraft move in the indicated direction, etc. The computer system also provides force feedback to the joystick, for example, when the aircraft is banking or accelerating in a turn or in other situations where the user may experience forces on the joystick or find it more difficult to steer the aircraft.

Figure 9:
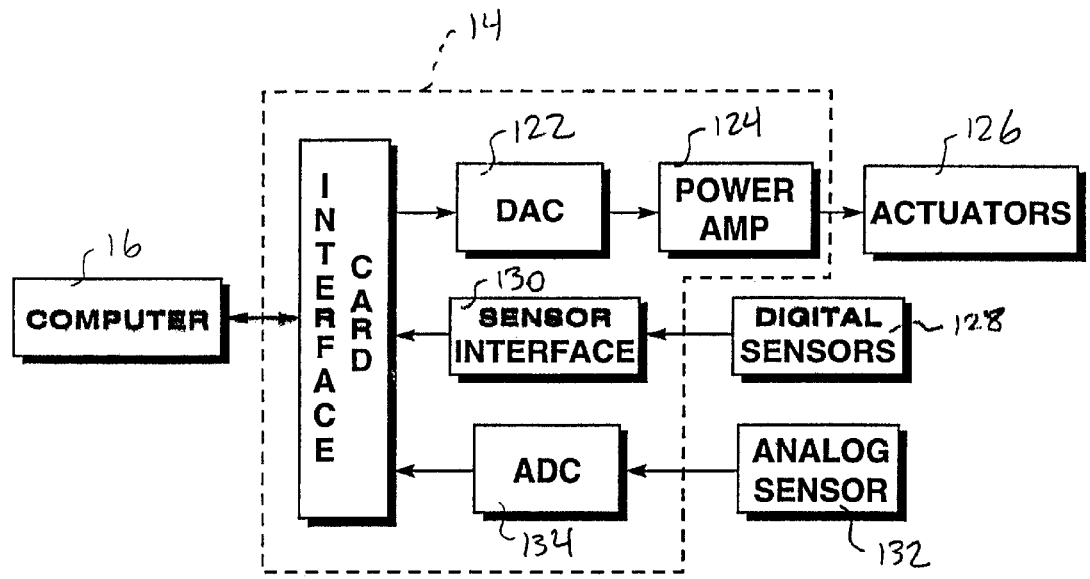
FIG. 9 is a block diagram of a computer and the interface between the computer and the mechanical apparatus of FIG. 2.

FIG. 9 is a schematic view of a computer 16 and an interface circuit 120 used in interface 14 to send and receive signals from mechanical apparatus 25. Circuit 120 includes computer 16, interface card 120, DAC 122, power amplifier circuit 124, digital sensors 128, and sensor interface 130. Optionally included are analog sensors 132 instead of or in addition to digital sensors 128, and ADC 134. In this embodiment, the interface 14 between computer 16 and mechanical apparatus 25 as shown in FIG. 1 can be considered functionally equivalent to the interface circuits enclosed within the dashed line in FIG. 14. Other types of interfaces 14 can also be used. For example, an electronic interface 14 is described in U.S. patent application Ser. No. 08/092,974, filed Jul. 16, 1993 and entitled "3-D Mechanical Mouse" assigned to the assignee of the present invention, which is the parent of continuation application Ser. No. 08/461,170, now U.S. Pat. No. 5,576,727, and incorporated herein by reference in its entirety. The electronic interface described therein was designed for the Immersion PROBE™ 3-D mechanical mouse and has six channels corresponding to the six degrees of freedom of the Immersion PROBE.

Interface card 120 is preferably a card which can fit into an interface slot of computer 16. For example, if computer 16 is an IBM AT compatible computer, interface card 14 can be implemented as an ISA or other well-known standard interface card which plugs into the motherboard of the computer and provides input and output ports connected to the main data bus of the computer.

Digital to analog converter (DAC) 122 is coupled to interface card 120 and receives a digital signal from computer 16. DAC 122 converts the digital signal to analog voltages which are then sent to power amplifier circuit 124. A DAC circuit suitable for use with the present invention is described with reference to FIG. 10. Power amplifier circuit 124 receives an analog low-power control voltage from DAC 122 and amplifies the voltage to control actuators 126. Power amplifier circuit 124 is described in greater detail with reference to FIG. 11. Actuators 126 are preferably DC servo motors incorporated into the transducers 66a, 66b, and 68, and any additional actuators, as described with reference to the embodiments shown in FIGS. 3, 7, and 8 for providing force feedback to a user manipulating object 44 coupled to mechanical apparatus 25.

Digital sensors 128 provide signals to computer 16 relating the position of the user object 44 in 3D space. In the preferred embodiments described above, sensors 128 are relative optical encoders, which are electro-optical devices that respond to a shaft's rotation by producing two phase-related signals. In the described embodiment, sensor interface circuit 130, which is preferably a single chip, receives the signals from digital sensors 128 and converts the two signals from each sensor into another pair of clock signals, which drive a bi-directional binary counter. The output of the binary counter is received by computer 16 as a binary number representing the angular position of the encoded shaft. Such circuits, or equivalent circuits, are well known to those skilled in the art; for example, the Quadrature Chip from Hewlett Packard, Calif. performs the functions described above.

Analog sensors 132 can be included instead of digital sensors 128 for all or some of the transducers of the present invention. For example, a strain gauge can be connected to stylus 130 of FIG. 7 to measure forces. Analog sensors 132 provide an analog signal representative of the position of the user object in a particular degree of motion. Analog to digital converter (ADC) 134 converts the analog signal to a digital signal that is received and interpreted by computer 16, as is well known to those skilled in the art.

Figure 10:
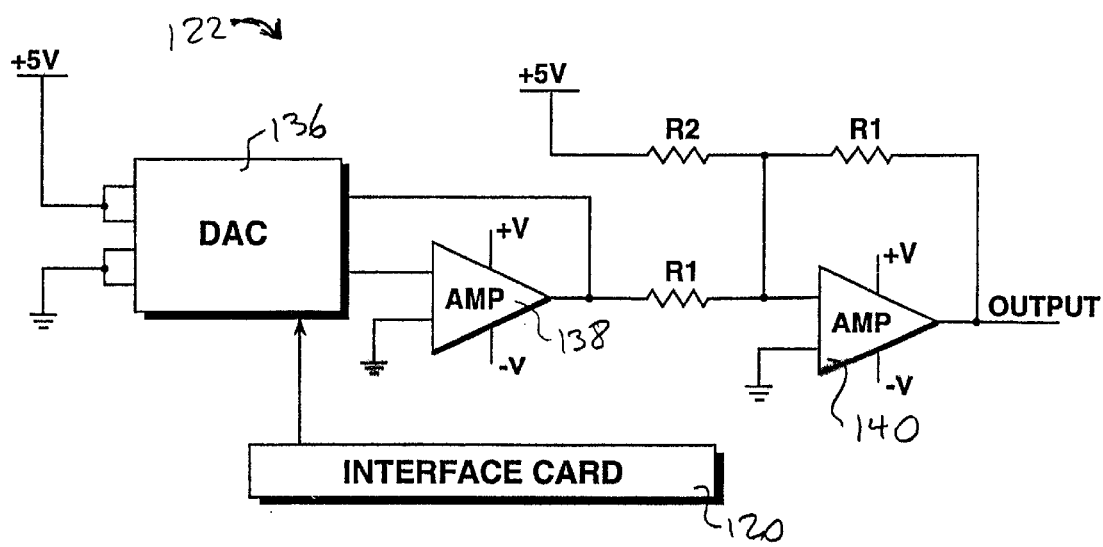
FIG. 10 is a schematic diagram of a suitable circuit for a digital to analog controller of the interface of FIG. 9.

FIG. 10 is a schematic view of a DAC circuit 122 of FIG. 9 suitable for converting an input digital signal to an analog voltage that is output to power amplifier circuit 124. In the described embodiment, circuit 122 includes a parallel DAC 136, such as the DAC1220 manufactured by National Semiconductor, which is designed to operate with an external generic op amp 138. Op amp 138, for example, outputs a signal from zero to −5 volts proportional to the binary number at its input. Op amp 140 is an inverting summing amplifier that converts the output voltage to a symmetrical bipolar range. Op amp 140 produces an output signal between −2.5 V and +2.5 V by inverting the output of op amp 138 and subtracting 2.5 volts from that output; this output signal is suitable for power amplification in amplification circuit 124. As an example, R1=200 kΩ and R2=400 kΩ. Of course, circuit 122 is intended as one example of many possible circuits that can be used to convert a digital signal to a desired analog signal.

Figure 11:
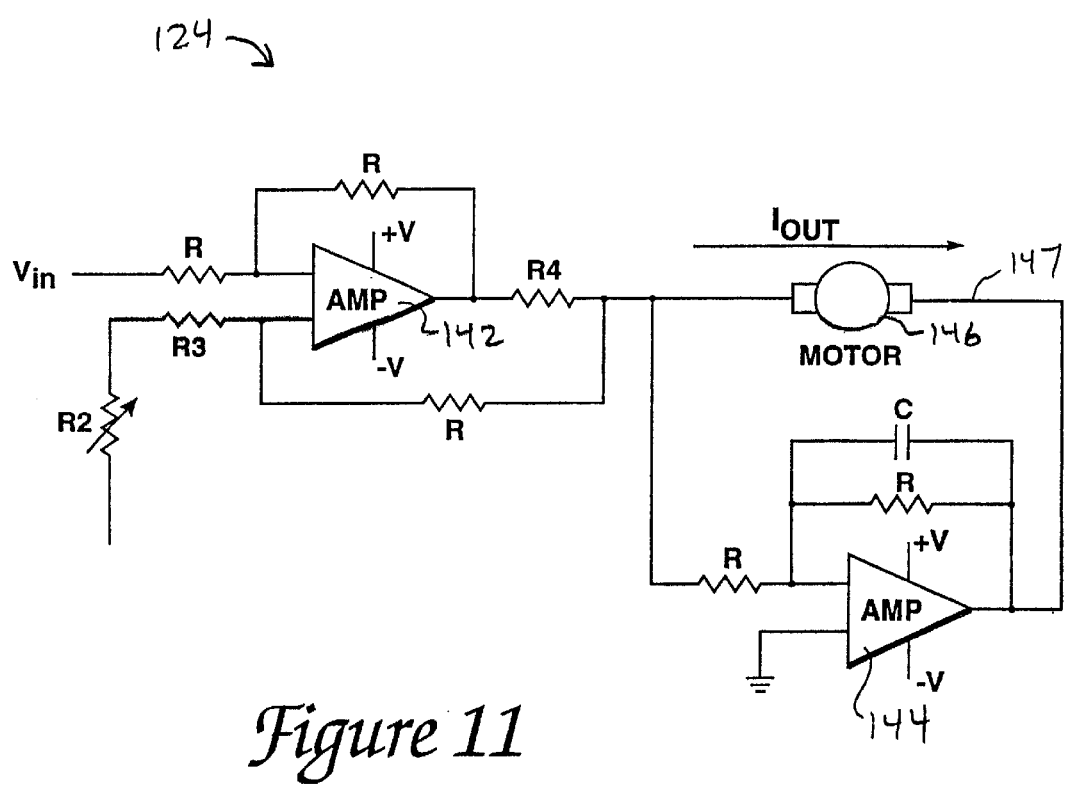
FIG. 11 is a schematic diagram of a suitable power amplification circuit for powering the actuators of the present invention as shown in FIG. 9.

FIG. 11 is a schematic view of a power amplifier circuit 124 suitable for use in the interface circuit 14 shown in FIG. 9. Power amplifier circuit receives a low power control voltage from DAC circuit 122 to control high-power, current-controlled servo motor 126. The input control voltage controls a transconductance stage composed of amplifier 142 and several resistors. The transconductance stage produces an output current proportional to the input voltage to drive motor 126 while drawing very little current from the input voltage source. The second amplifier stage, including amplifier 144, resistors, and a capacitor C, provides additional current capacity by enhancing the voltage swing of the second terminal 147 of motor 146. As example values for circuits 124, R=10 kΩ, R2=500 Ω, R3=9.75 kΩ, and R4=1 Ω. Of course, circuit 124 is intended as one example of many possible circuits that can be used to amplify voltages to drive actuators 126.

Figure 12A:
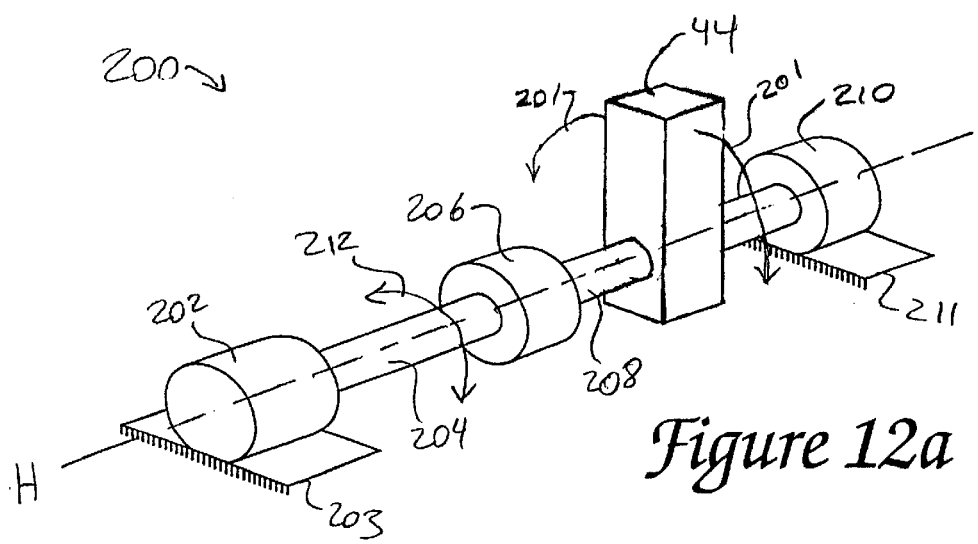
FIG. 12a is a schematic diagram of a transducer system in accordance with the present invention.

FIG. 12a is a schematic diagram of a transducer system 200 suitable for use with the present invention. Transducer system 200 is ideally suited for an interface system in which passive actuators, instead of active actuators, are implemented. As shown in FIG. 12a, transducer system 200 is applied to a mechanism having one degree of freedom, as shown by arrows 201. Embodiments in which system 200 is applied to systems having additional degrees of freedom are described subsequently. Transducer system 200 includes an actuator 202, an actuator shaft 204, a non-rigidly attached coupling 206, a coupling shaft 208, a sensor 210, and an object 44.

Actuator 202 transmits a force to object 44 and is preferably grounded, as shown by symbol 203. Actuator 202 is rigidly coupled to an actuator shaft 204 which extends from actuator 202 to non-rigidly attached coupling 206. Actuator 202 provides rotational forces, shown by arrows 212, on actuator shaft 204. In the preferred embodiment, actuator 202 is a passive actuator which can apply a resistive or frictional force (i.e., drag) to shaft 204 in the directions of arrow 212 but cannot provide an active force to shaft 204 (i.e., actuator 202 cannot cause shaft 204 to rotate). Thus, an external rotational force, such as a force generated by a user, is applied to shaft 204, and passive actuator 202 provides resistive forces to that external rotational force. Preferred passive actuators include rotary magnetic brakes, and, in particular, magnetic particle brakes, which are low cost and power-efficient devices. Suitable magnetic particle brakes can be obtained from Force Limited, Inc. of Santa Monica, Calif.

Passive actuators can provide realistic force feedback to a user operating an interface apparatus in a simulated environment. Passive actuators impose a resistance to the motion of an object 44 manipulated by the user. Thus, a user who manipulates an interface having passive actuators will feed forces only when he or she actually moves an object of the interface.

passive actuators 202 provide several advantages when compared to active actuators. A substantially lower current is required to drive passive actuators than active actuators. This allows a less expensive power supply to drive a passive actuator system, and allows a force feedback mechanism to be smaller and more lightweight due to the smaller power supply. In addition, passive actuators require substantially slower control signals to operate effectively in a simulation environment than do active actuators such as motors. This is significant if the controller of an interface mechanism is a computer system that includes only a standard, low-speed input/output port, such as a serial port. Serial ports are quite common to personal computers but do not communicate quickly enough to perform real-time, stable control of most active actuators. When using a controller with slower control signals, passive actuators can provide stable force feedback to the user. Another advantage of passive actuators, as explained above, is that passive actuators do not generate forces on the interface and the user and are thus more safe for the user.

Coupling 206 is coupled to actuator shaft 204. Actuator 202, actuator shaft 204, and coupling 206 can be considered to be an "actuator assembly" or, in a passive actuator system, a "braking mechanism." Coupling 206 is preferably not rigidly coupled to actuator shaft 204 and thus allows an amount (magnitude) of "play" between actuator shaft 204 and coupling 206. The term "play", as used herein, refers to an amount of free movement or "looseness" between a transducer and the object transduced, so that, for instance, the object can be moved a short distance by externally-applied forces without forces without being affected by forces applied to the object by an actuator. In the preferred embodiment, the user can move the object a short distance without fighting the drag induced by a passive actuator such as a brake. For example, actuator 202 can apply a resistive or frictional force to actuator shaft 204 so that actuator shaft 204 is locked in place, even when force is applied to the shaft. Coupling 206, however, can still be freely rotated by an additional distance in either rotational direction due to the play between coupling 206 and shaft 204. This play is intentional for purposes that will be described below, and is thus referred to as a "desired" amount of play. Once coupling 206 is rotated to the limit of the allowed play, it either forces shaft 204 to rotate with it further; or, if actuator 202 is holding (i.e., locking) shaft 204, the coupling cannot be further rotated in that rotational direction. The amount of desired play between actuator 202 and object 44 greatly depends on the resolution of the sensor 210 being used, and is described in greater detail below. Examples of types of play include rotary backlash, such as occurs in gear systems as described in the above embodiments, and compliance or torsion flex, which can occur with flexible, rotational and non-rotational members. Embodiments including these forms of play are described in greater detail below with reference to FIGS. 13 and 16, respectively.

Coupling shaft 208 is rigidly coupled to coupling 206 and extends to sensor 210. Sensor 210 is preferably rigidly coupled to coupling shaft 208 so as to detect rotational movement of shaft 208 and object 44 about axis H. Sensor 210 preferably provides a electrical signal indicating the rotational position of shaft 208 and is preferably grounded as indicated by symbol 211. In the described embodiment, sensor 210 is a digital optical encoder, similar to the encoders described in the above embodiments of FIGS. 1–11. In alternate embodiments, sensor 210 can be separated from object 44, coupling shaft 208, and coupling 206. For example, a sensor having an emitter and detector of electromagnetic energy might be disconnected from the rest of transducer system 200 yet be able to detect the rotational position of object 44 using a beam of electromagnetic energy, such as infrared light. Similarly, a magnetic sensor could detect the position of object 44 while being uncoupled to shaft 208 or object 44. The operation of such sensors are well-known to those skilled in the art.

Sensor 210 has a sensing resolution, which is the smallest change in rotational position of coupling shaft 208 that the sensor can detect. For example, an optical encoder of the described embodiment may be able to detect on the order of about 3600 equally-spaced "pulses" (described below) per revolution of shaft 208, which is about 10 detected pulses per degree of rotational movement. Thus, the sensing resolution of this sensor is about 1/10 degree in this example. Since it is desired to detect the desired play between actuator 202 and object 44 (as described below), this desired play should not be less than the sensing resolution of sensor 210 (e.g., 1/10 degree). Preferably, the desired play between actuator and object would be at least 1/5 degree in this example, since the encoder could then detect two pulses of movement, which would provide a more reliable measurement and allow the direction of the movement to be more easily determined.

Sensor 210 should also be as rigidly coupled to shaft 208 as possible so that the sensor can detect the desired play of shaft 208 and object 44. Any play between sensor 210 and object 44 should be minimized so that such play does not adversely affect the sensor's measurements. Typically, any inherent play between sensor 210 and object 44 should be less than the sensing resolution of the sensor, and preferably at least an order of magnitude less than the sensing resolution. Thus, in the example above, the play between sensor and object should be less than 1/10 degree and preferably less than 1/100 degree. Use of steel or other rigid materials for shaft 208 and other components, which is preferred, can allow the play between sensor 210 and object 44 to be made practically negligible for purposes of the present invention. As referred to herein, a sensor that is "rigidly" coupled to a member has a play less than the sensing resolution of the sensor (preferably a negligible amount). The play between actuator 202 and object 44 is described in greater detail below. A suitable encoder to be used for sensor 210 is the "Softpot" from U.S. Digital of Vacouver, Wash.

Object 44 is rigidly coupled to coupling shaft 208. Object 44 can take a variety of forms, as described in previous embodiments, and can be directly coupled to coupling shaft 208 or can be coupled through other intermediate members so shaft 208. In FIG. 12a, object 44 is coupled to shaft 208 between coupling 206 and sensor 210. Thus, as object 44 is rotated about axis H, shaft 208 is also rotated about axis H and sensor 210 detects the magnitude and direction of the rotation of object 44. Alternatively, object 44 can be coupled directly to coupling 206. Coupling 206 and/or shafts 204 and 208 can be considered a "play mechanism" for providing the desired play between actuator 202 and object 44. Certain suitable objects 44 include a joystick, medical instrument (catheter, laparscope, etc.), a steering wheel (e.g. having one degree of freedom), a pool cue, etc.

As stated above, transducer system 200 is ideally suited for mechanical systems that include low-cost elements such as passive actuators. If a controlling computer system, such as computer system 16, is to provide accurate force feedback to an object being held and moved by a user, the computer system should be able to detect the direction that the user is moving the object even when the passive actuators are being applied to the object at maximum force to lock the object in place. However, this can be difficult when using passive actuators, because passive rotary actuators provide a resistive force or friction to motion in both rotational directions about an axis. Thus, when force from an actuator prevents movement of an object in one direction, it also prevents movement in the opposite direction. This typically does not allow the computer to sense movement of the object in the opposite direction, unless the user provides a greater force than the actuator's resistive force and overcomes the actuator's force (i.e., overpowers the actuator).

For example, object 44 is a one-degree-of-freedom joystick used for moving a video cursor that moves in the direction indicated by the joystick on a video screen. The user moves the cursor into a virtual (computer generated) "wall", which blocks the motion of the cursor in one direction. The controlling computer system also applies force feedback to the joystick by activating passive magnetic particle brakes to prevent the user from moving the joystick in the direction of the wall, thus simulating the surface of the wall. If sensor 210 is rigidly coupled to actuator shaft 204, a problem occurs if the user wishes to move the joystick in the opposite direction to the wall. Since the brakes have locked the joystick in both directions, the computer cannot detect when the user switches the joystick's direction unless the user overpowers the passive brakes. Thus, to the user, the cursor feels like it is "stuck" to the wall.

Applicant's introduced ("desired") play between object 44 and actuator 202 solves this problem effectively and inexpensively. The play allows the joystick or other connected object to be moved slightly in the opposite direction even when the brakes are applied with maximum friction to the joystick. The sensor, being rigidly attached to the joystick, is not locked by the actuator and detects the change in direction. The sensor relays the movement to the computer, which deactivates the brakes to allow the joystick to be moved freely in the opposite direction. If the user should move the cursor into the wall again, the brakes would be similarly activated. A method for controlling actuator 202 in such a virtual reality environment is described with reference to FIG. 22.

Active actuators, such as the DC motors described in the above embodiments of FIGS. 3–8 or other types of motors, can also be used with transducer system 200. Many active actuators, however, can apply force in one selected direction in a degree of freedom, so that the deliberately-introduced play would not be necessary when using such actuators.

In alternate embodiments, linear play can be implemented instead of rotary play. The preferred embodiments of FIGS. 12a and 12b (described below) implement play among rotational components, such as a rotary actuator and sensor. However, compliance or backlash can also be implemented between linearly moving (i.e., translatable) components. For example, a small amount of space can be provided between interlocked translatable components to provide play in accordance with the present invention. An actuator and sensor for transducing linear movement, which are well-known to those skilled in the art, can be used in such an embodiment.

Other devices or mechanisms besides the use of play can be used in other embodiments to detect the direction of motion of object 44 while passive actuators are holding the object in place. For example, force sensors can be coupled to the object to measure the force applied to the object by the user along desired degrees of freedom. A force sensor can detect if a user is applying a force, for example, towards the virtual wall or away from the virtual wall, and the computer can activate or deactivate the passive actuators accordingly. Deliberately-introduced play between object and actuators is thus not required in such an embodiment. However, such force sensors can be expensive and bulky, adding to the cost and size of the interface mechanism.

Figure 12B:
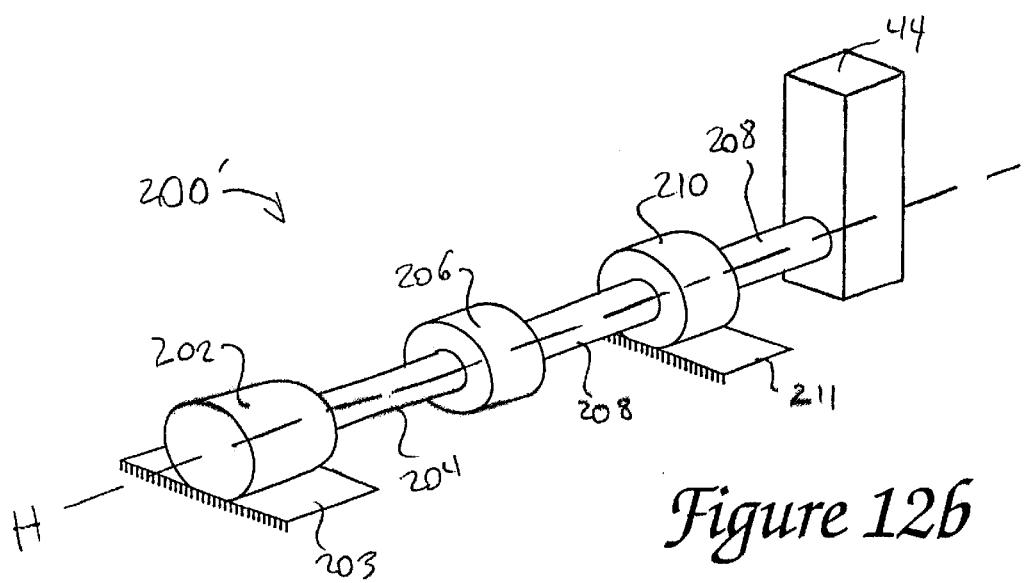

FIG. 12b is a schematic diagram of an alternate transducer system 200' similar to transducer system 200 shown in FIG. 12a. In this embodiment, sensor 210 is positioned between coupling 206 and object 44 on coupling shaft 208. Shaft 208 extends through sensor 210 and can be rigidly coupled to object 44 at the end of the shaft. Transducer system 200' functions substantially the same as transducer system 200 shown in FIG. 12a.

FIG. 13 is a schematic view of a preferred embodiment of transducer system 200 for a mechanism providing one degree of freedom that uses rotary backlash to provide play between actuator 202 and coupling 206. Keyed actuator shaft 214 is rigidly coupled to actuator 202 and mates with keyed coupling 216. The cross-sectional diameter of keyed actuator shaft 214 is preferably smaller than bore 218 of coupling 216, to provide the desired backlash, as described in greater detail with reference to FIG. 14a. Coupling shaft 208, sensor shaft 210, and object 44 are substantially similar to these components as described with reference to FIG. 12a. In alternate embodiments, backlash can be provided between actuator 202 and coupling 206 using different components, such as gears, pulleys, etc.

FIG. 14a is a side sectional view of keyed actuator shaft 214 and coupling 216 taken along line 14a—14a in FIG. 13. Keyed shaft 214 extends into keyed bore 218 of coupling 216. In FIG. 14a, gap 220 is provided around the entire perimeter of shaft 214. In alternate embodiments, gap 220 can be provided only between the sides of the keyed portion 222 of shaft 214, as described with reference to FIG. 15.

FIG. 14b is a side sectional view of keyed actuator shaft 214 and coupling 216 taken along line 14b—14b of FIG. 14a. Keyed shaft 214 is shown partially extending into coupling 216. As shown in FIG. 14a, a small gap 220 is preferably provided between coupling 216 and shaft 214. When shaft 214 is rotated, coupling 216 is also rotated after the keypad portion of shaft 214 engages the keyed portion of bore 218, as described with reference to FIG. 15. Coupling shaft 208 rotates as coupling 216 rotates, since it is rigidly attached.

FIG. 15 is a detailed view of FIG. 14a showing the keyed portions of shaft 214 and bore 218. Extended keyed portion 222 of shaft 218 protrudes into receiving keyed portion 224 of bore 218. In alternate embodiments, an extended keyed portion of coupling 216 can protrude into a receiving keyed portion of shaft 214. Gap 220 has a width d which determines how much desired backlash (play) is introduced between actuator 202 and object 44. (Additional unintentional backlash or other inherent play can exist between the components of the system due to compliance of the shafts, etc.) In the desired embodiment, in which sensor 210 has a sensing resolution of about 1/10 degree, d is preferably about 1/1000 inch. Note that the distance d can widely vary in alternative embodiments. The chosen distance d is preferably made small enough to prevent the user from feeling the backlash that exists in the system when handling object 44 and yet is large enough for the sensor to detect the play (i.e., greater than the sensing resolution of sensor 210) to allow the sensor to inform the computer the direction that the user is moving object 44. Thus, the distance d is highly dependent on the sensing resolution of sensor 210. For example, if a sensing resolution of 1/100 degree is available, the distance d can be much smaller. The amount of backlash that a user can typically feel can depend on the size and shape of object 44; however, the backlash described above is not detectable by a user for the majority of possible objects. In other embodiments, it may be desirable to allow the user to feel the backlash to other play in the system, and thus a greater distance d can be implemented.

In the preferred embodiment, distance d allows rotational movement of coupling 216 at least equal to the sensing resolution of sensor 210 in either direction, thus allowing a total backlash of distance of 2d between surfaces 228 and 232 of coupling 216. Alternatively, a total backlash of distance d between surfaces 228 and 232 can be implemented (half of the shown distance). In such an embodiment, however, sensor 210 would only be able to detect movement from one limit of the backlash to the other limit, and, for example, movement of coupling 216 from a center position (as shown in FIG. 15) would not be detected.

In the described embodiment, digital encoder sensors 210 are used, in which rotational movement is detected using a number of divisions on a wheel that are rotated past fixed sensors, as is well known to those skilled in the art. Each division causes a "pulse", and the pulses are counted to determine the amount (magnitude) of movement. Distance d can be made as large or larger than the sensing resolution of the encoder so that the magnitude and direction of the movement within gap 220 can be detected. Alternatively, the resolution of the sensor can be made great enough (i.e., the distance between divisions should be small enough, in a digital encoder) to detect movement within gap 220. For example, two or more pulses should be able to be detected within distance d to determine the direction of movement of object 44 and coupling 216 using a digital encoder or the like.

When coupling 216 is initially rotated from the position shown in FIG. 15 in a direction indicated by arrow 226 (counterclockwise in FIG. 14a) as the user moves object 44, the coupling freely rotates. Coupling 216 can no longer be rotated when the inner surface 228 of keyed portion 224 engages surface 230 of keyed portion 222. Thereafter, external force (such as from the user) in the same direction will cause either both coupling 216 and shaft 214 to rotate in the same direction, or the external force will be prevented if actuator 202 is locking shaft 214 in place with high resistive force to prevent any rotational movement of shaft 214.

If the user suddenly moves object 44 in the opposite rotational direction after surface 228 has engaged surface 230, coupling 216 can again be rotated freely within gap 220 until surface 232 of bore 218 engages surface 234 of shaft 214, at which point both shaft and coupling are rotated (or no rotation is allowed, as described above). It is the magnitude and direction of the movement between the engagement of the surfaces of keyed portions 222 and 224 which can be detected by sensor 210, since sensor 210 is rigidly coupled to coupling 216. Since sensor 210 can relay to the controlling computer the direction which coupling 216 (and thus object 44) is moving, the computer can deactivate or activate actuator 202 accordingly. Even if object 44 is held in place by actuator 202, as when moving into a virtual "wall", the computer can detect the backlash movement of object 44 if the user changes the direction of the object and can release the brakes accordingly. It should be noted that computer 16 should preferably deactivate (release) the passive actuator before surface 232 engages surface 234 so that the user will not feel any resistance to movement in the opposite direction.

Figure 16:
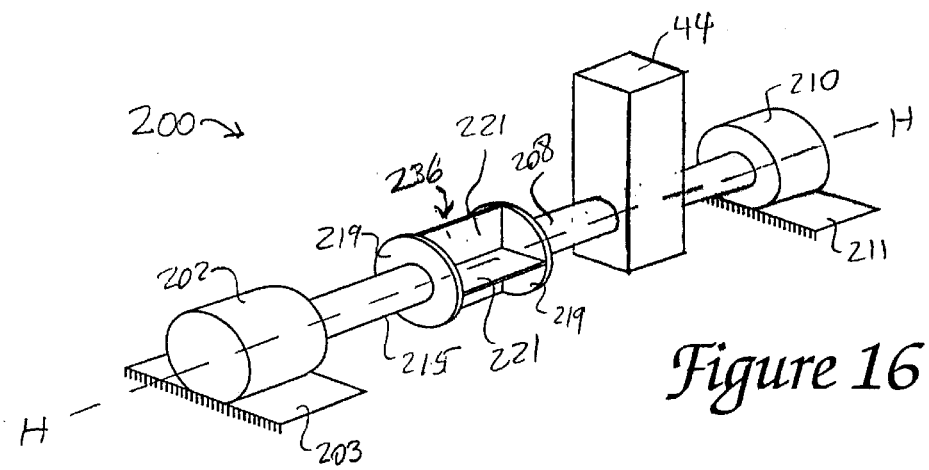
FIG. 16 is a schematic diagram of the transducer system of FIG. 12a having a flexible coupling.

FIG. 16 is a schematic diagram of an alternate embodiment of transducer system 200 in which the desired play between actuator 202 and object 44 is provided by a flexible (i.e. compliant) coupling instead of the keyed shaft system with backlash shown in FIG. 13. A flexible coupling can take many possible forms, as is well known to those skilled in the art. The flexible coupling allows coupling shaft 208 to rotate independently of actuator shaft 204 for a small distance, then forces actuator shaft 204 to rotate in the same direction as coupling shaft 208, as described with reference to FIGS. 13–15. In FIG. 16, actuator 202, coupling shaft 208, sensor 210 and object 44 are similar the equivalent components as discussed above with reference to FIG. 12a. A flexible coupling 236 has two ends 219 and lengthwise portions 221 that provide torsion flex between the ends 219. Flexible coupling 236 thus allows an amount of torsion flex (play) about axis H between coupling shaft 208 and actuator shaft 215. When actuator shaft 215 is locked in place by actuator 202, coupling shaft 208 is rotated, and coupling 236 has been flexed to its limit in one rotational direction, shaft 208 will be prevented from rotating in the same direction and the user will be prevented from moving object 44 further in that direction. If object 44 and coupling shaft 208 were caused to suddenly rotate in the opposite direction, coupling 236 would flex freely in that direction and this movement would be detected by sensor 210, allowing the computer to change resistive force applied by actuator 202 accordingly. When coupling 236 reached maximum flexibility in the other direction, the mechanism would perform similarly and the user would feel forces (if any) from actuator 202. Compliance or flex can also be provided with spring members and the like.

Similar to the backlash system described in FIGS. 13–15, the amount of play provided by flexible coupling 236 between actuator 202 and object 44 is equal to or greater than the sensing resolution of sensor 210. A typical flexible coupling has an inherent amount of stiffness so that a force must be applied to overcome the stiffness. Preferably, the flexible coupling 236 has a low stiffness and flexes with a small amount of force with respect to the maximum drag output by the passive actuator 202. Flexible coupling 236 also preferably has a small amount of flex to provide a small amount of desired play; as above, the desired play when using flexible coupling 236 should be the minimum amount of play that the sensor 210 can reliably detect.

Figure 17:
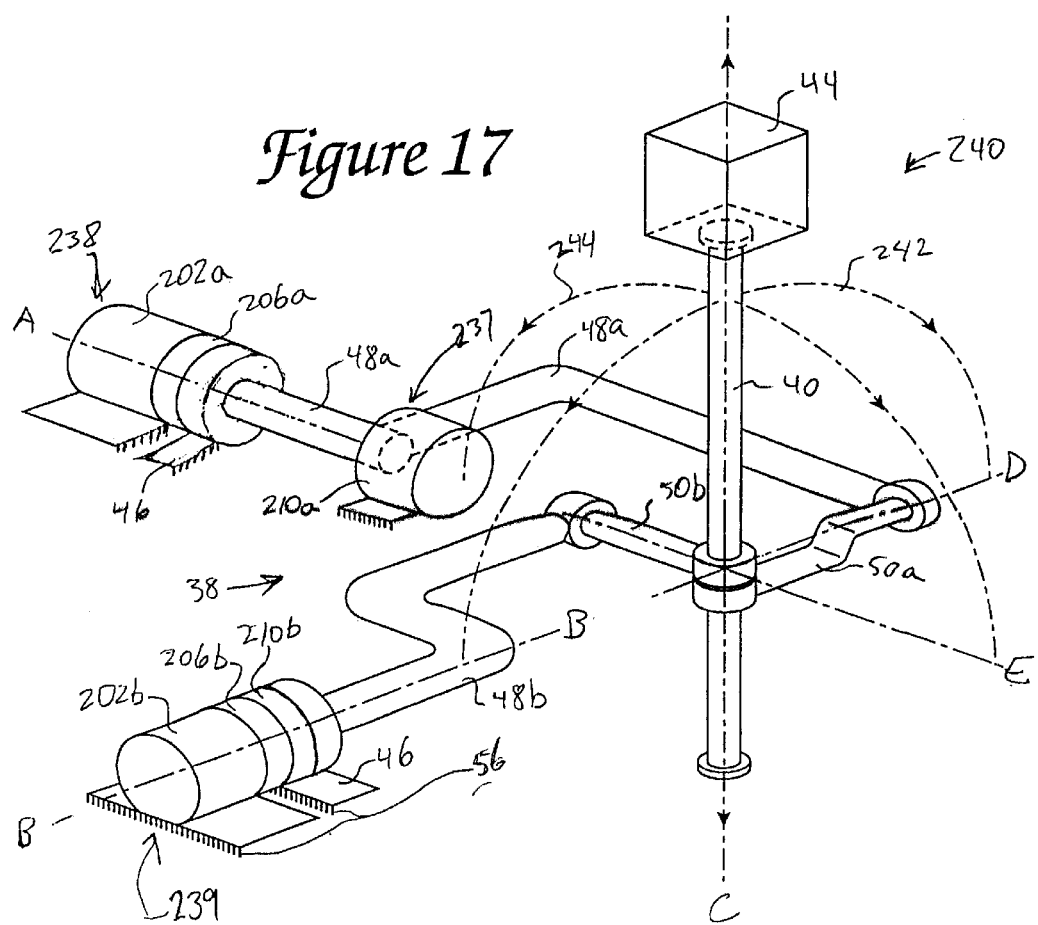
FIG. 17 is a schematic diagram of the transducer systems of FIGS. 12a and 12b coupled to the mechanical apparatus of FIG. 2.

FIG. 17 is a schematic diagram of an embodiment of a mechanical apparatus 240 using transducer system 200. Similar to apparatus 25 as described with reference to FIG. 2, apparatus 200 includes a gimbal mechanism 38 and linear axis member 40. A user object 44 is preferably coupled to linear axis member 40. Gimbal mechanism 38 provides two revolute degrees of freedom as shown by arrows 242 and 244. Linear axis member 40 provides a third linear degree of freedom as shown by arrows 246. These components function as described with reference to FIG. 2. Coupled to each extension member 48a and 48b is a transducer system 238 (equivalent to transducer system 200) and 239 (equivalent to transducer system 200'), respectively. It should be noted that the two different embodiments of transducer system 200 and 200' are shown on one mechanical apparatus 240 for illustrative purposes. Typically, only one embodiment of system 200 or 200' is used for both ground members 48a and 48b.

Transducer system 238 is similar to the system shown in FIG. 12a wherein object 44 is positioned between coupling 206 and sensor 210. Transducer system 238 includes actuator 202a, which is grounded and coupled to coupling 206a (ground 56 is schematically shown coupled to ground member 46, similar to FIG. 2). Coupling 206a is coupled to extension member 48a which ultimately connects to object 44 and provides a revolute degree of freedom about axis A. Sensor 210a is rigidly connected to extension member 48a at the first bend 237 in the extension member. Sensor 210a is also grounded by either coupling it to ground member 46 or separately to ground 56. Sensor 210a thus detects all rotational movement of extension member 48a and object 44 about axis A. However, coupling 206a provides a desired amount of play between actuator 202a and extension member 48a as described above. Alternatively, sensor 210a can be rigidly coupled to extension member 48a at other positions or bends in member 48a, or even on central member 50b, as long as the rotation of object 44 about axis A is detected.

Transducer system 239 is similar to the transducer system shown in FIG. 12b in which sensor 210 is positioned between coupling 206 and object 44. Actuator 220b is grounded and is non-rigidly coupled (i.e., coupled with the desired play as described above) to coupling 206b. Coupling 206b is rigidly coupled, in turn, to sensor 210b, which separately grounded and rigidly coupled to ground member 46 (leaving coupling 206b ungrounded). Extension member 48b is also rigidly coupled to coupling 206b by a shaft extending through sensor 210b (not shown). Sensor 210b thus detects all rotational movement of extension member 48b and object 44 about axis B. Coupling 206b provides a desired amount of play between actuator 202b and extension member 48b for reasons described above.

Rotational resistance or impedance can thus be applied to either or both of extension members 48a and 48b and object 44 using actuators 202a and 202b. Couplings 206a and 206b allow computer 16 to sense the movement of object 44 about either axis A or B when actuators are locking the movement of object 44. A similar transducer system to system 238 or 239 can also be provided for linear axis member 40 to sense movement in and provide force feedback to the third degree of freedom along axis C. Such a system can be implemented similarly to the transducers shown in FIG. 6 and as described below.

Figure 18:
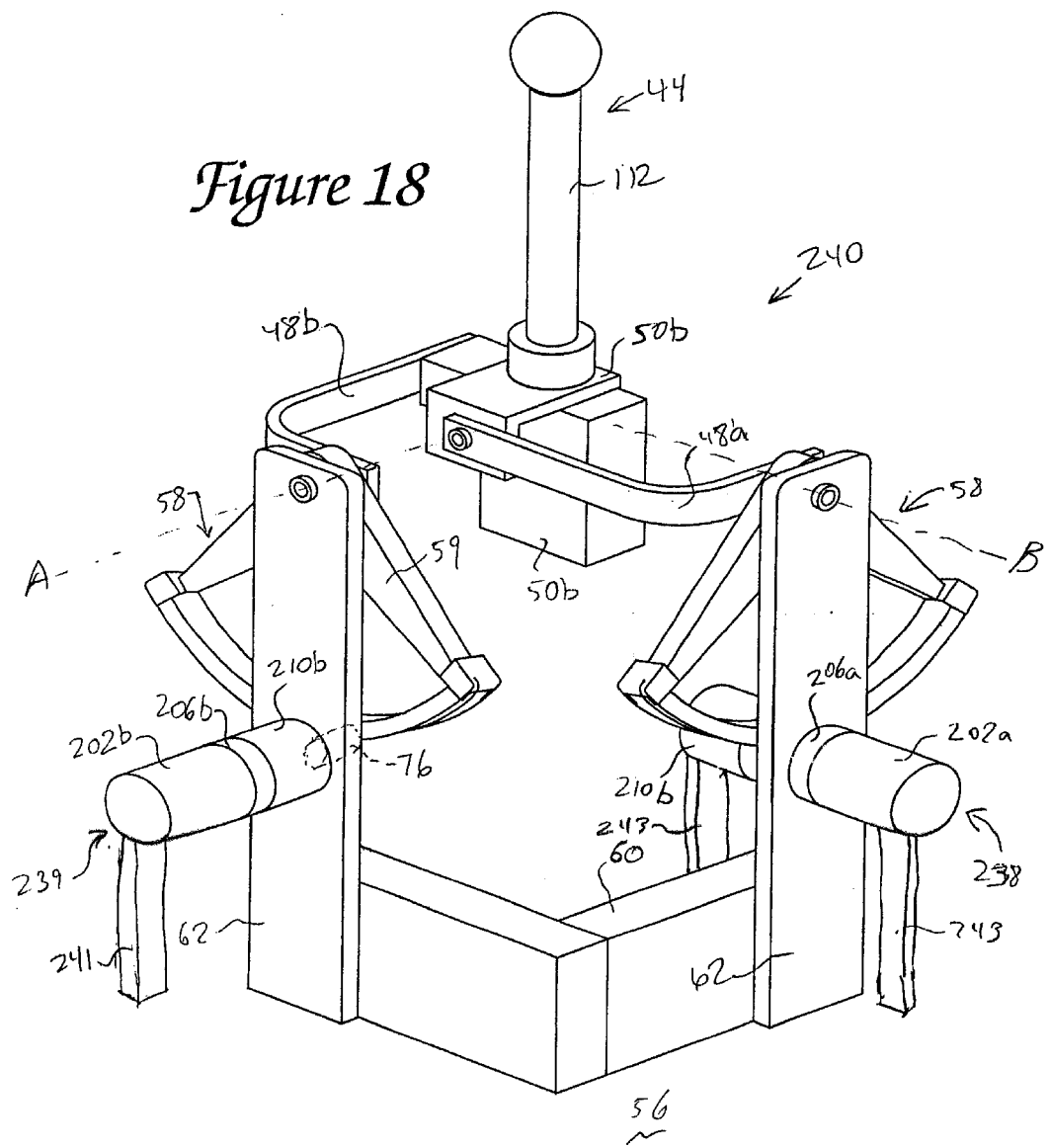
FIG. 18 is a perspective view of the transducer systems of FIGS. 12a and 12b coupled to the mechanical apparatus of FIG. 8.

FIG. 18 is a perspective view of a preferred embodiment of mechanical apparatus 240 shown in FIG. 17. Apparatus 20 is similar to the embodiment of apparatus 25''' shown in FIG. 8 above, in which object 44 is implemented as a joystick 112 movable in two degrees of freedom about axes A and B. For illustrative purposes, apparatus 240 is shown with two embodiments of transducer system 200 and 200'. System 239 is shown similarly as in FIG. 17 and includes actuator 202b, coupling 206b, and sensor 210b, with the appropriate shafts connecting these components not shown. Actuator 220b is grounded by, for example, a support member 241. The coupling shaft 208 extending from sensor 210b is preferably coupled to capstan pulley 76 of capstan drive mechanism 58. When object 44 is moved about axis A, extension member 48b is also moved, which causes capstan member 59 (which is rigidly attached to member 48b) to rotate. This movement causes pulley 76 to rotate and thus transmits the motion to the transducer system 239. As described above with reference to FIG. 5, the capstan mechanism allows movement of object 44 without substantial backlash. This allows the introduced, controlled backlash of coupling 206 to be the only backlash in the system. In addition, as described previously, the capstan drive mechanism provides a mechanical advantage for the movement of object 44. Sensor 210b can thus detect rotation at a higher resolution and actuator 202b can provide greater forces to object 44. This can be useful when, for example, a user can overpower the resistive forces output by actuator 202b; capstan mechanism 58 allows greater forces to be output from an actuator that are more difficult for the user to overcome. A different type of gearing system can also be used to provide such mechanical advantage, such as a pulley system. Transducer system 239 or 238 can also be directly connected to ground member 46 and extension member 48a or 48b, as shown in FIG. 17. For example, transducer system 239 can be directly coupled to vertical support 62 and capstan member 59 on axis A. However, in such a configuration, the described benefits of the capstan drive mechanism would not be gained.

Transducer system 238 is shown coupled to the other extension member 48a similarly as in FIG. 17. In this configuration, actuator 202a and coupling 206a are positioned on one side of vertical support member 62. Coupling shaft 208 preferably extends through vertical support member 62 and pulley 76 and is coupled to sensor 210a, which is grounded. Transducer system 238 gains the advantages of the capstan drive mechanism as described above. Alternatively, sensor 210b can be coupled to capstan member and vertical support 62 at axis B; however, the sensor would gain no mechanical advantage from the capstan drive mechanism 58 at this location. Actuator 202a and sensor 210b are preferably grounded by, for example, support members 243.

Transducer systems 238 and 239 can also be used with other apparatuses as shown in the embodiments of FIGS. 3 and 7. For example, a third linear degree of freedom and a fourth rotational degree of freedom can be added as shown in FIG. 3. Transducer systems 238 or 239 can be used to sense movement in and provide force feedback to those third and fourth degrees of freedom. Similarly, transducer system 238 or 239 can be applied to the fifth and sixth degrees of freedom as shown and described with reference to FIG. 7.

Figure 19:
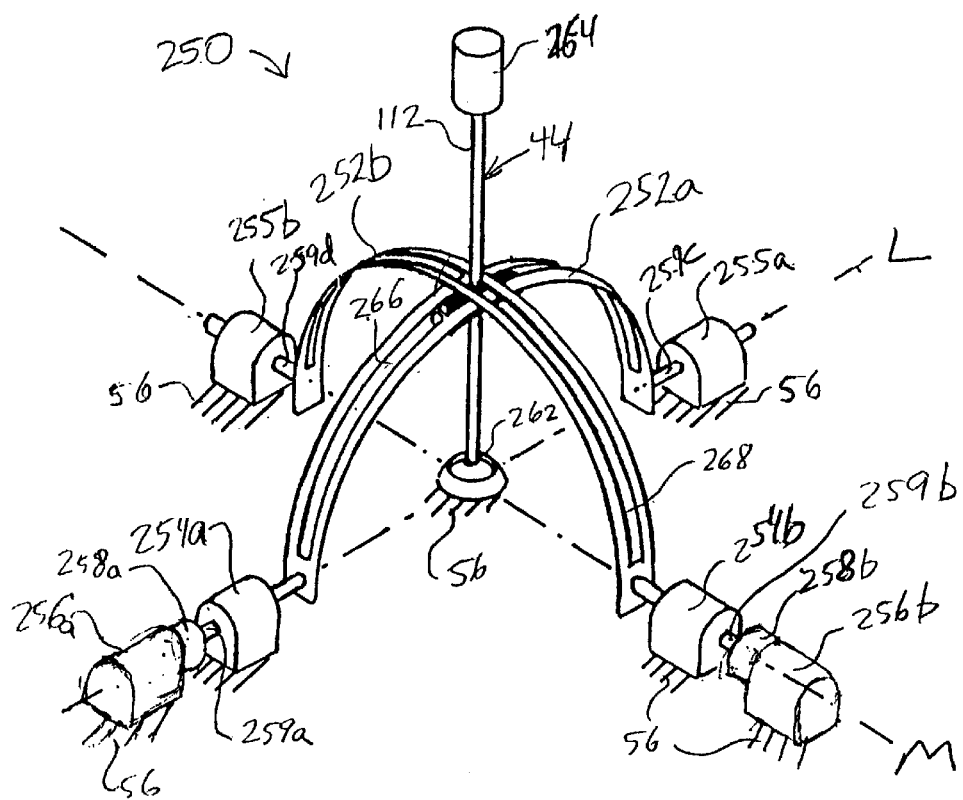
FIG. 19 is a perspective view of a slotted yoke mechanical apparatus used with the transducer system of FIG. 12a or 12b.

FIG. 19 is a perspective view of alternate interface apparatus 250 suitable for use with transducer system 200. Mechanism 250 includes a slotted yoke configuration for use with joystick controllers that is well-known to those skilled in the art. Apparatus 250 includes slotted yoke 252a, slotted yoke 252b, sensors 254a and 254b, bearings 255a, and 255b, actuators 256a and 256b, couplings 258a and 258b, and joystick 44. Slotted yoke 252a is rigidly coupled to shaft 259a that extends through and is rigidly coupled to sensor 254a at one end of the yoke. Slotted yoke 252a is similarly coupled to shaft 259c and bearing 255a at the other end of the yoke. Slotted yoke 252a is rotatable about axis L and this movement is detected by sensor 254a. Coupling 254a is rigidly coupled to shaft 259a and is coupled to actuator 256 such that a desired amount of play is allowed between actuator 265 and shaft 259a. This arrangement permits the play between object 44 and the actuator as described in the above embodiments. Actuator 256a is preferably a passive actuator such as magnetic particle brakes. In alternate embodiments, actuator 256a and coupling 258a can be instead coupled to shaft 259c after bearing 255a. In yet other embodiments, bearing 255a and be implemented as another sensor like sensor 254a.

Similarly, slotted yoke 252b is rigidly coupled to shaft 259b and sensor 254b at one end and shaft 259d and bearing 255b at the other end. Yoke 252b can rotated about axis M and this movement can be detected by sensor 254b. A coupling 258b is rigidly coupled to shaft 259b and an actuator 256b is coupled to coupling 258b such that a desired amount of play is allowed between shaft 259b and actuator 256b, similar to actuator 256a described above.

Object 44 is a joystick 112 that is pivotally attached to ground surface 260 at one end 262 so that the other end 264 typically can move in four 90-degree directions above surface 260 (and additional directions in other embodiments). Joystick 112 extends through slots 266 and 268 in yokes 252a and 252b, respectively. Thus, as joystick 112 is moved in any direction, yokes 252a and 252b follow the joystick and rotate about axes L and M. Sensors 254a–d detect this rotation and can thus track the motion of joystick 112. The addition of actuators 256a and 256b allows the user to experience force feedback when handling joystick 44. The couplings 258a and 258b provide an amount of play, as described above, to allow a controlling system to detect a change in direction of joystick 112, even if joystick 112 is held in place by actuators 256a and 256b. Note that the slotted yoke configuration typically introduces some inherent play (such as compliance or backlash) to the mechanical system. Couplings 259a and 259b can be added to provide an additional amount of play, if desired. Similarly, other interface apparatuses that typically provide an amount of inherent play can be used such that the inherent play is measured by sensor 210 and no coupling 206 is required. Also, other types of objects 44 can be used in place of joystick 112, or additional objects can be coupled to joystick 112.

In alternate embodiments, actuators and couplings can be coupled to shafts 259c and 259d to provide additional force to joystick 112. Actuator 256a and an actuator coupled to shaft 259c can be controlled simultaneously by a computer or other electrical system to apply or release force from bail 252a. Similarly, actuator 256b and an actuator coupled to shaft 259d can be controlled simultaneously.

Figure 20:
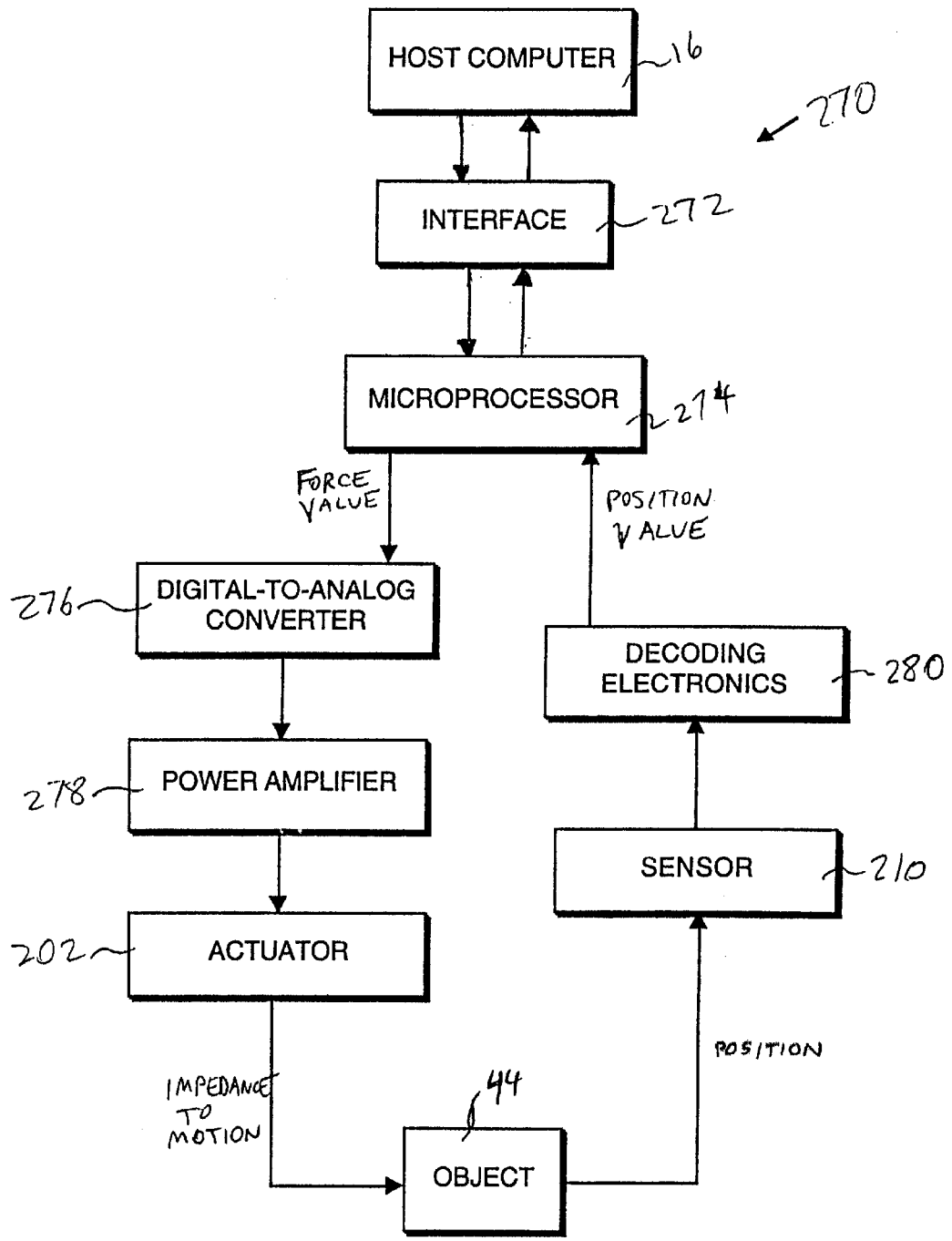
FIG. 20 is a block diagram showing an interface for a mechanical apparatus having the transducer system of FIG. 12a or 12b.

FIG. 20 is a block diagram 270 of an electronic interface suitable for use with the transducer system 200. The electronic components in diagram 270 are preferably used with passive actuators and optical encoder sensors. The interface of diagram 270, however, can also be used with other embodiments of interface apparatus 25 as described above.

Host computer 16 can be computer system 16 as described above with reference to FIGS. 1 and 9 and is preferably implements a simulation or similar virtual environment which a user is experiencing and moving object 44 in response to, as is well known to those skilled in the art. Host computer 16 includes interface electronics 272. In the described embodiment, interface electronics include a serial port, such as an RS-232 interface, which is a standard interface included on most commercially available computers. This interface is different than the interface card and electronics shown with respect to FIG. 9 above, which allows faster control signal transmission and is thus more suitable for controlling active actuators than the presently described interface electronics.

Microprocessor 274 can be used to control input and output signal that are provided to and from interface 272. For example, microprocessor can be provided with instructions to wait for commands or requests from computer host 16, decode the command or request, and handle input and output signals according to the command or request. If computer 16 sends a command to control actuators, microprocessor 274 can output signals to the actuator representing the force to be applied by the actuator, and can send an acknowledgment to computer 16 that such output was sent. If computer 16 sends a request for sensory input, microprocessor 274 can read position data from the sensors and send this data to the computer 16. Suitable microprocessors for use as microprocessors 274 includes the MC68HC711E9 by Motorola and the PIC16C74 by Microchip.

Digital-to-analog converter (DAC) 276 is electrically coupled to microprocessor 274 and receives digital signals representing a force value from the microprocessor. DAC 276 converts the digital signal to analog signal as is well known to those skilled in the art. A suitable DAC is the MAX530ACNG manufactured by Maxim. Power amplifier 278 receives the analog signal from DAC 276 and converts the signal into an appropriate brake control signal for actuator 202. For example, an LM324 and TIP31 can be used as power amplifier 278. Actuator 202, which is preferably a magnetic particle brake by Force Limited, Inc., receives the brake signal and provides appropriate resistive forces to impede the motion of object 44 caused by the user. Preferably, a separate DAC and power amplifier is used for each actuator 202 implemented in the interface apparatus so the computer 16 can control each actuator separately for each provided degree of motion.

Sensor 210 is preferably a digital optical encoder which operates as described above; for example, a suitable encoder is the "Softpot" from U.S. Digital of Vacouver, Wash. The sensor detects the position of object 44 and provides a digital position signal to decoding electronics 280, which convert the sensor signal into an input signal suitable to be interpreted by computer 16. For example, quadrature decoder LS7166 is suitable to decode quadrature signals from sensor 210. The position value signals are interpreted by computer 16 which updates the virtual reality environment and controls actuator 202 as appropriate. Other interface mechanisms other than decoding electronics 280 can also be used to provide an appropriate signal to microprocessor 274. In alternate embodiments, an analog sensor 210 can be used to provide an analog signal to an analog-to-digital converter (ADC), which can provide a digital position signal to computer 16. The resolution of the detected motion of object 44 would then be limited by the resolution of the ADC.

However, noise can sometimes mask small movements of object 44 from an analog sensor 210, which can potentially mask the play that is important to the present embodiment of the invention.

Figure 21:
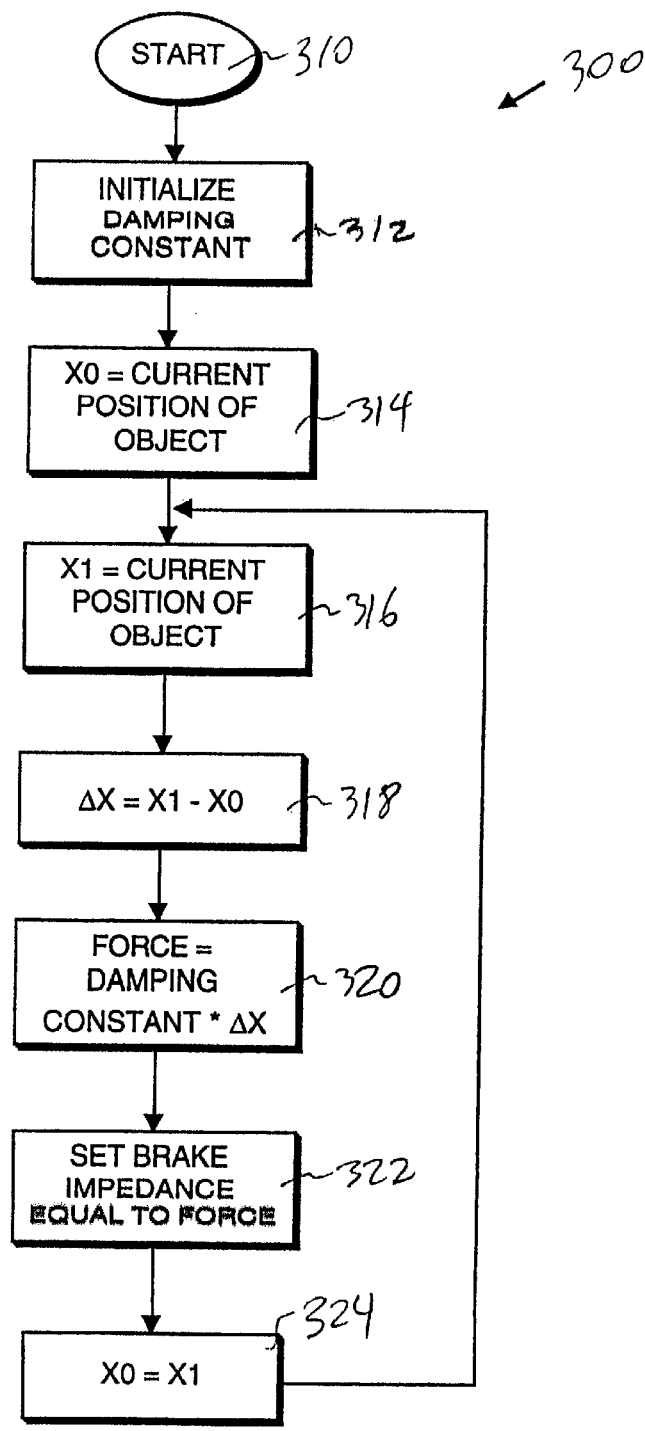
FIG. 21 is a flow diagram illustrating a method for controlling an actuator of the transducer system of FIG. 12a or 12b in the simulation of a fluid environment.

FIG. 21 is a flow diagram illustrating the control process 300 of actuator 202 during an example of simulated motion of object 44 along one degree of freedom through a fluid or similar material. Process 300 can be implemented by computer 16 or by microprocessor 274 in conjunction with computer 16. The process starts at 310, and, in step 312, a damping constant is initialized. This constant indicates the degree of resistance that object 44 experiences when moving through a simulated material, where a greater number indicates greater resistance. For example, water would have a lower damping constant than oil or syrup.

In step 314, the current position of object 44 along the examined degree of freedom is stored in a variable X0. In step 316, the current position of object 44 along the examined degree of freedom is stored in a variable X1. When process 300 is initially implemented, X0 and X1 are set to the same value. In step 318, a variable ΔX is set to the difference between X1 and X0 (which is zero the first time implementing the process). From the sign (negative or positive) of ΔX, the direction of the movement of object 44 can also be determined. In next step 320, a variable FORCE is set equal to the damping constant multiplied by ΔX. A signal representative of the value of FORCE is then set to the brake (or other passive actuator) in step 322 to set the brake impedance at the desired level. In step 324, variable X0 is set equal to X1, and the process then returns to step 316 to read and store another position of object 44 in variable X1. Process 300 thus measures the manual velocity of object 44 as controlled by the user and produces a brake impedance (FORCE) proportional to the user's motion to simulate movement through a fluid. Movement in other mediums, such as on a bumpy surface, on an inclined plane, etc., can be simulated in a similar fashion using different methods of calculating FORCE.

Figure 22:
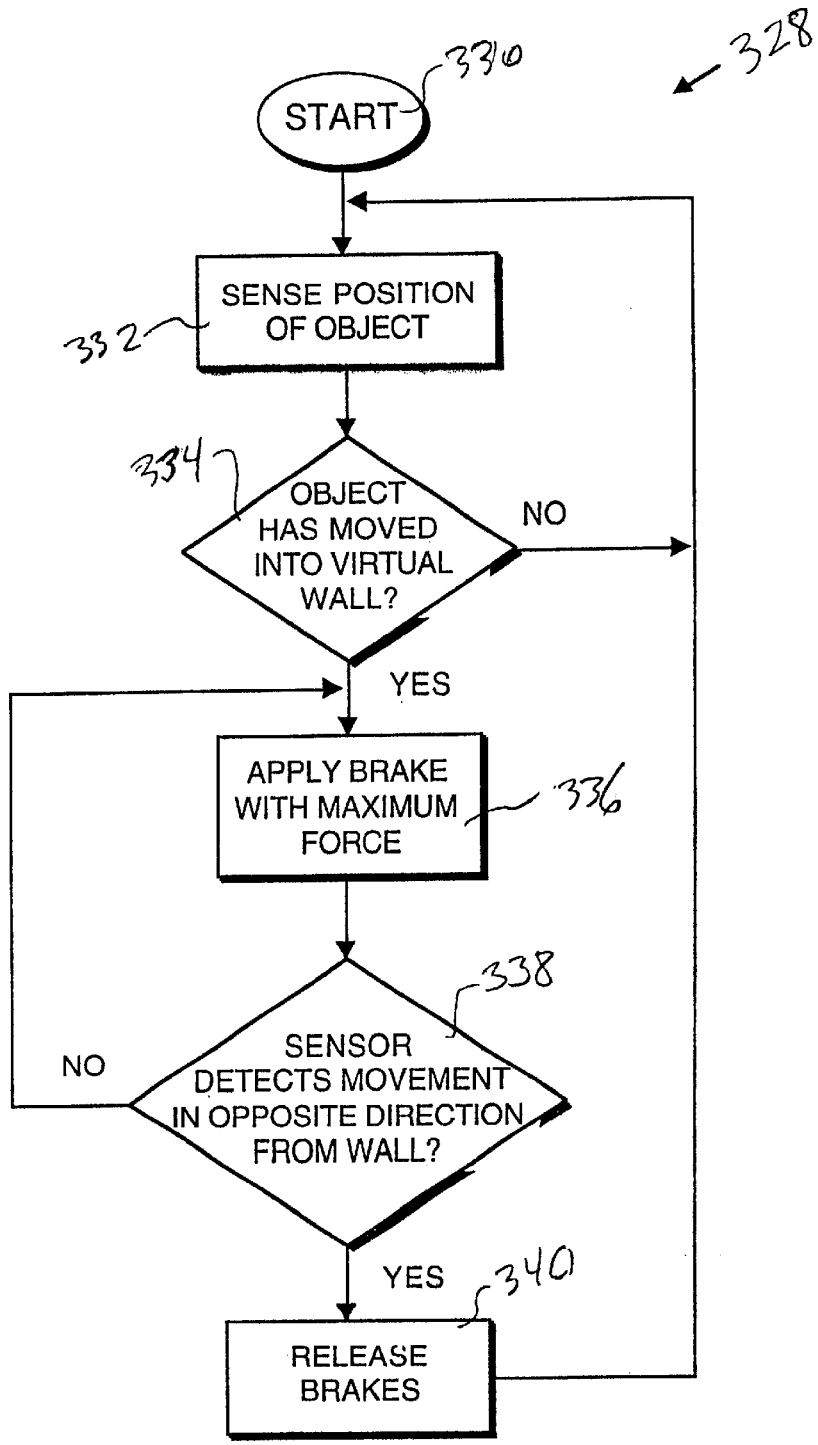
FIG. 22 is a flow diagram illustrating a method for controlling an actuator of the transducer system of FIG. 12a or 12b when encountering an obstacle in a virtual environment.

FIG. 22 is a flow diagram 328 illustrating a preferred method of modelling a "wall" or other hard surface or obstruction in a virtual environment when using a mechanical interface such as interface 240 or interface 250 with transducer system 200. It is assumed for this method that an object 44 is being grasped and moved by a user in a virtual environment. A computer system 16 is preferably detecting the position of the object and providing force feedback to the object when appropriate.

The method starts at 330, and, in a step 332, the position of an object is sensed by the computer 16 and/or microprocessor 274. Sensors 210 provide the rotary and/or linear position of object 44 in the number of degrees of freedom being sensed. The computer 16 updates a virtual reality environment in response to the user's movements of object 44. For example, if the user moves a steering wheel object 44, the computer 16 can move the point of view of the user as if looking out a vehicle and turning the vehicle. It should be noted that the computer 16/microprocessor 274 can be providing force feedback to the user that is not related to the virtual wall in this step as well. For example, the computer can cause a joystick to require greater force to be moved when simulating a vehicle moving in mud, over a bumpy surface, etc., as described above with reference to FIG. 21.

In step 334, it is determined if object 44 (or a virtual, computer-generated object controlled by object 44) has been moved into a virtual wall or a similar obstruction that can prevent object 44 from moving in one or more directions. If the object has not been moved into such an obstruction, step 272 is repeated and any other appropriate force feedback according to the object's movement can be applied. If the object has been moved into such an obstruction, then step 336 is implemented, in which the passive actuator such as a brake provides maximum impedance to the motion of object 44 along the obstructed degree(s) of freedom. This feels to the user as if the object 44 has hit an obstruction and can no longer be moved in the direction of the "wall" or obstacle.

In next step 338, the computer 16 checks for any movement in direction opposite to the wall. If no movement in this direction is sensed by sensors 210, then continued maximum resistive force is applied to object 44 in step 336; the user is thus still forcing object 44 towards the wall. If the computer/microprocessor detects movement away from the wall in step 338, due to the play caused by coupling 206, then step 340 is implemented, in which the computer/microprocessor releases the brakes before the limit to the play is reached in the new direction (i.e., within the allowed compliance of backlash). The user can thus freely move object 44 away from the wall without feeling like it is stuck to the wall. The process then returns to step 332, in which the computer/microprocessor senses the position of object 44.

While this invention has been described in terms of several preferred embodiments, it is contemplated that alterations, modifications and permutations thereof will become apparent to those skilled in the art upon a reading of the specification and study of the drawings. For example, the linked members of apparatus 25 can take a number of actual physical sizes and forms while maintaining the disclosed linkage structure. In addition, other gimbal mechanisms can also be provided with a linear axis member 40 to provide three degrees of freedom. Likewise, other types of gimbal mechanisms or different mechanisms providing multiple degrees of freedom can be used with the capstan drive mechanisms disclosed herein to reduce inertia, friction, and backlash in a system. A variety of devices can also be used to sense the position of an object in the provided degrees of freedom and to drive the object along those degrees of freedom. In addition, the sensor and actuator used in the transducer system having desired play can take a variety of forms. Similarly, other types of couplings can be used to provide the desired play between the object and actuator. Furthermore, certain terminology has been used for the purposes of descriptive clarity, and not to limit the present invention. It is therefore intended that the following appended claims include all such alterations, modifications and permutations as fall within the true spirit and scope of the present invention.

What is claimed is:

1. An apparatus for interfacing the motion of an object with an electrical system, the apparatus comprising:

a support mechanism providing a first revolute degree of freedom to said object about a first axis of rotation;

a sensor electrically coupled to said electrical system and mechanically coupled to said support mechanism for sensing positions of said object along said first degree of freedom, said sensor having a sensing resolution; and a braking mechanism electrically coupled to said electrical system and mechanically coupled to said support mechanism to create a drag along said first degree of freedom, said braking mechanism providing an amount of play between said braking mechanism and said object along said degree of freedom, said amount of play being equal to or greater than said sensing resolution;

whereby said braking mechanism and said sensor provide an electromechanical interface between said object and said electrical system.

2. An apparatus as recited in claim 1 wherein said support mechanism provides a second degree of freedom to said object about a second axis of rotation, and further comprising a sensor for sensing positions of said object along said second degree of freedom and a braking mechanism to create a drag along said second degree of freedom.

3. An apparatus as recited in claim 2 further comprising a capstan drive mechanism coupled between said braking mechanism and said support mechanism, said capstan drive mechanism transmitting said drag generated by said braking mechanism to said support mechanism and transmitting movement of said object to said sensor.

4. An apparatus as recited in claim 3 wherein said braking mechanism includes an actuator and a coupling, said coupling providing said amount of play.

5. An apparatus as recited in claim 4 further comprising a linear axis member coupled to said support mechanism at said intersection of said two axes of rotation capable of being translated along a third axis in a third degree of freedom, wherein said object is coupled to said linear axis member and is translatable along said third axis.

6. An apparatus as recited in claim 5 further comprising a third degree of freedom transducer coupled between said support mechanism and said linear axis member to create a drag along said third degree of freedom and sense translation of said linear axis member.

7. An apparatus as recited in claim 4 wherein said support mechanism includes a closed loop five member linkage.

8. An apparatus as recited in claim 7 wherein said object includes one of the group consisting of at least a portion of a surgical tool, a stylus, and a joystick.

9. An apparatus as recited in claim 2 wherein said electrical system includes a digital processing system.

10. An apparatus as recited in claim 8 wherein said braking mechanism includes magnetic particle brakes.

11. An apparatus as recited in claim 7 wherein said five member linkage includes:
a ground member coupled to a ground surface;
first and second extension members, each extension member being coupled to said ground member;
first and second central members, said first central member having an end coupled to said first extension member and said second central member having an end coupled to said second extension member, wherein said central members are coupled to said linear axis member at ends not coupled to said extension members.

12. An apparatus as recited in claim 1 further comprising an active actuator electrically coupled to said electrical system and mechanically coupled to said support mechanism to create a force in said first degree of freedom.

13. An apparatus for interfacing the motion of an object with a computer system, the apparatus comprising:
a support mechanism providing a first degree of freedom to said object;
a sensor electrically coupled to said computer system and mechanically coupled to said support mechanism operative to sense positions of said object in said first degree of freedom, said sensor having a sensing resolution;
a drag mechanism electrically coupled to said computer system and rigidly mechanically coupled to said support mechanism to create a drag along said first degree of freedom, said drag mechanism providing an amount of play between said drag mechanism and said object in said degree of freedom, said amount of play being equal to or greater than said sensing resolution; and
an active actuator electrically coupled to said computer system and mechanically coupled to said support mechanism to create a force in said first degree of freedom based on electrical signals received by said active actuator.

14. An apparatus as recited in claim 13 wherein said first degree of freedom is a rotary degree of freedom.

15. An apparatus as recited in claim 13 wherein said support mechanism provides a second degree of freedom to said object and further comprising a sensor for sensing positions of said object in said second degree of freedom and a drag mechanism to create a drag in said second degree of freedom.

16. An apparatus as recited in claim 13 wherein said drag mechanism includes an actuator and a coupling, said coupling providing said amount of play.

17. An apparatus as recited in claim 13 wherein said support mechanism includes a closed loop five member linkage.

18. An apparatus as recited in claim 13 wherein said drag mechanism includes a magnetic particle brake.

19. An interface apparatus for interfacing the motion of an object with a computer system, the apparatus comprising:
a sensor operative to sense positions of said object in a first degree of freedom, said positions provided to said computer system, said sensor having a sensing resolution;
a passive actuator operative to create a drag to said motion of said object in said first degree of freedom;
a play mechanism providing an amount of play between said passive actuator and said object in said degree of freedom, said amount of play being equal to or greater than said sensing resolution; and
an active actuator operative to create an active force on said object in said first degree of freedom based on electrical signals received by said active actuator.

20. An interface apparatus as recited in claim 19 further comprising a support mechanism providing said first degree of freedom to said object.

21. An interface apparatus as recited in claim 19 wherein said first degree of freedom is a rotary degree of freedom.

22. An interface apparatus as recited in claim 20 wherein said support mechanism provides a second degree of freedom to said object and further comprising a sensor for sensing positions of said object in said second degree of freedom and a passive actuator to create a drag in said second degree of freedom.

23. An interface apparatus as recited in claim 19 further comprising a linear axis member coupled to said support mechanism at an intersection of two axes of rotation of said first and second degrees of freedom, said linear axis member capable of being translated along a third axis in a third degree of freedom, wherein said object is coupled to said linear axis member and is translatable along said third axis.

24. An interface apparatus as recited in claim 20 wherein said support mechanism includes a closed loop five member linkage.

25. An interface apparatus as recited in claim 19 wherein said object includes one of the group consisting of at least a portion of a surgical tool, a stylus, and a joystick.

26. An interface apparatus as recited in claim 19 wherein said passive actuator includes a magnetic particle brake.

* * * * *